United States Patent
Sutcliffe et al.

(10) Patent No.: US 6,635,479 B1
(45) Date of Patent: Oct. 21, 2003

(54) HYPOTHALAMUS-SPECIFIC POLYPEPTIDES

(75) Inventors: J. Gregor Sutcliffe, Cardiff, CA (US); Kaare M. Gautvik, Oslo (NO); Luis De Lecea, Del Mar, CA (US); Floyd E. Bloom, San Diego, CA (US); Patria E. Danielson, San Diego, CA (US); Vigdis T. Gautvik, Oslo (NO); Thomas S. Kilduff, Menlo Park, CA (US); Pamela E. Foye, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/230,896

(22) PCT Filed: Aug. 1, 1997

(86) PCT No.: PCT/US97/13657

§ 371 (c)(1),
(2), (4) Date: Feb. 2, 1999

(87) PCT Pub. No.: WO98/05352

PCT Pub. Date: Feb. 12, 1998

Related U.S. Application Data

(60) Provisional application No. 60/023,220, filed on Aug. 2, 1996.

(51) Int. Cl.[7] .................. C07H 21/04; C12N 15/00; C12N 15/09; C12N 5/00; C12N 5/02
(52) U.S. Cl. ................. 435/325; 435/320.1; 536/23.1; 536/23.5
(58) Field of Search ................ 536/23.1, 22.1, 536/23.5; 530/300, 350; 435/320.1, 325

(56) References Cited

U.S. PATENT DOCUMENTS 5,969,123 A * 10/1999 Holtzman ............... 536/23.1

OTHER PUBLICATIONS

Lee et al., Comparative expressed–sequence–tag analysis of differential gene expression profiles in PC–12 cells before and after nerve growth factor treatment. PNAS (USA) 92:8303–8307 (1995).
Cho et al., Characterization of a rat cDNA clone encoding calcium/calmodulin–dependent protein kinase I. Biochimica et Biophysica Acta 1224(1):156–160 (1994).
Charnock–Jones et al., Extension of incomplete cDNAs (ESTs) by biotin/strepavidin–mediated walking using the polymerase chain reaction. J. Biotechnology 35(2–3):205–215 (1994).
Fehmann et al., Cell and molecular biology of the incretin hormones glucagon–like peptide–I and glucose–dependent insulin releasing polypeptide. Endocrine Reviews 16(3):390–410 (1995).
Hudson T. Human STS WT–10041. GENBANK Accession No. G11664. Oct. 19, 1995.

* cited by examiner

Primary Examiner—Anne-Marie Falk
(74) Attorney, Agent, or Firm—Olson & Hierl, Ltd.

(57) ABSTRACT

Disclosed are hypocretin polynucleotides and hypocretin polypeplides, as well as antibodies, oligonucleotides, diagnostic kits and methods, and therapeutic compositions and methods. Hypocretin, one of several novel liypothalamic-specific polypeptides identified isolated and sequenced, is localized to regions of the hypothalamus involved in appetite and feeding behavior. Hypocretin polypeptides are biologically active, producing electrical changes in neurons, lowering body temperature and reducing food intake.

6 Claims, 10 Drawing Sheets

```
consensus:                             RL  LL    GNHAAGILT G
hcrt1:      LGVDAQPLPDCCRQKTCSCRLYELLHGAGNHAAGILTLG
hcrt2:             PGPPGLQGRLQRLLQANGNHAAGILTMG
SECRETIN:   HSDGTFTSKLSRLRDSARLQRLLQGLV HSDGTFTSK
                       * ********    ** ** *
```

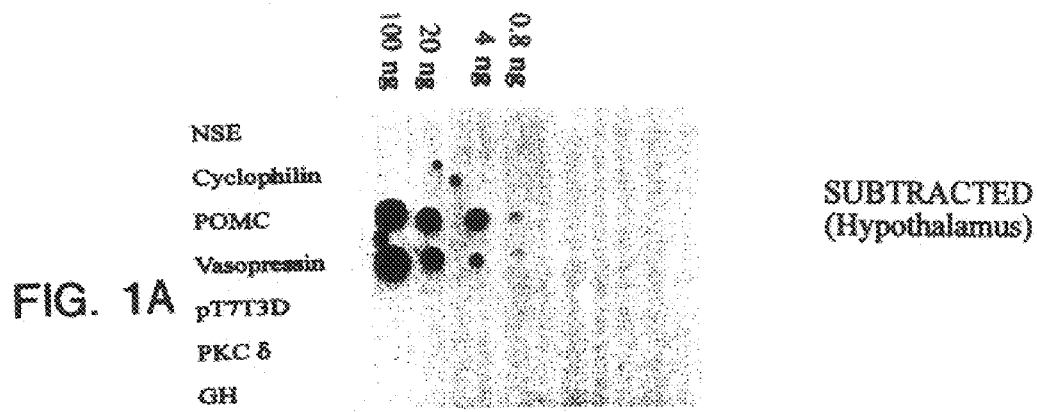
FIG. 1A SUBTRACTED (Hypothalamus)
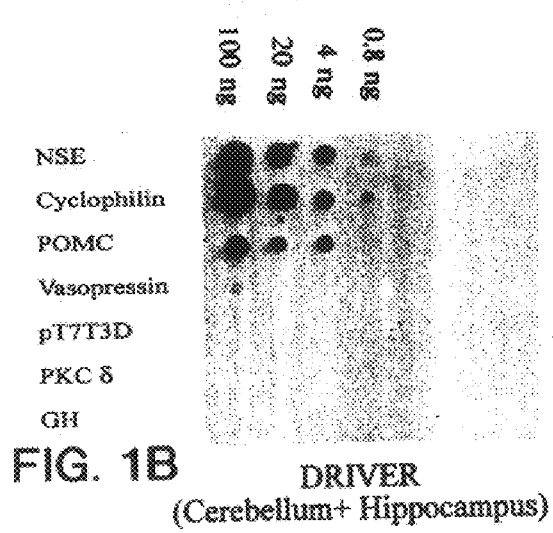
FIG. 1B DRIVER (Cerebellum+ Hippocampus)
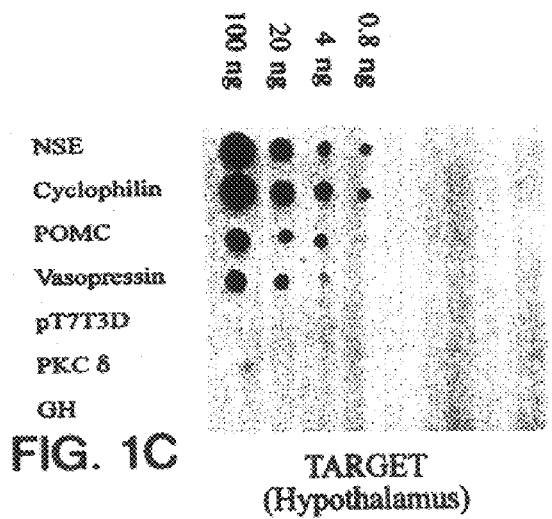
FIG. 1C TARGET (Hypothalamus)

D1 D2 T

D1 D2 T

D1 D2 T

D1 D2 T

Clone 2

Clone 35

Clone 6

Clone 10

Clone 12

Clone 20

Clone 67

FIG. 3C
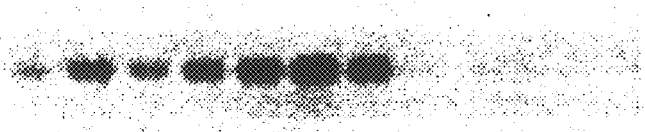
Clone 3
Clone 15
Clone 29
FIG. 3D
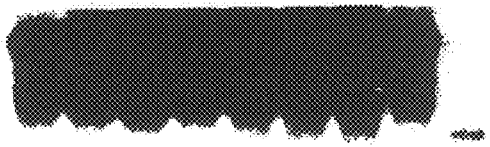
Clone 21
Clone 37
Clone 98
Clone 99
Cyclophilin

FIG. 5A

```
M   N   L/F P   S   T   K   V   P   W   A   A   V   T   L   L
ATG AAC CTT CCT TCT ACA AAG GTT CCC TGG GCC GCC GTG ACG CTG CTG
ATG AAC TTT CCT TCT ACA AAG GTT CCC TGG GCC GCC GTG ACG CTG CTG
            *
L   L   L   L   L   P   P   A   L   L   S   L   G   V   D   A
CTG CTG CTA CTG CTG CCG CCG GCG CTG CTG TCG CTT GGG GTG GAC GCG
CTG CTG CTA CTG CTG CCA CCG GCG CTG CTG TCG CTT GGG GTG GAC GCA
                                                            *
Q   P   L   P   D   C   C   R   Q   K   T   C   S   C   R   L
CAG CCT CTG CCC GAC TGC TGT CGC CAG AAG ACG TGT TCC TGC CGT CTC
CAG CCT CTG CCC GAC TGC TGT CGC CAG AAG ACG TGT TCC TGC CGT CTC

Y   E   L   L   H   G   A   G   N   H   A   A   G   I   L   T
TAC GAA CTG TTG CAC GGA GCT GGC AAC CAC GCC GCG GGC ATC CTC ACT
TAC GAA CTG TTG CAC GGA GCT GGC AAC CAC GCT GCG GGT ATC CTG ACT
                                        *       *       *
L   G   K   R   R   P   G   P   P   G   L   Q   G   R   L   Q
CTG GGA AAG CGG CGA CCT GGA CCC CCA GGC CTC CAA GGA CGG CTG CAG
CTG GGA AAG CGG CGG CCT GGA CCT CCA GGC CTC CAG GGA CGG CTG CAG
                *           *               *
R   L   L   Q   A   N   G   N   H   A   A   G   I   L   T   M
CGC CTC CTT CAG GCC AAC GGT AAC CAC GCA GCT GGC ATC CTG ACC ATG
CGC CTC CTT CAG GCC AAC GGT AAC CAC GCA GCT GGC ATC CTG ACC ATG

G   R   R   A   G   A   E   L   E   P   Y/H P   C   P/S G   R
GGC CGC CGC GCA GGC GCA GAG CTA GAG CCA TAT CCC TGC CCT GGT CGC
GGC CGC CGC GCA GGC GCA GAG CTA GAG CCA CAT CCC TGC TCT GGT CGC
                                            *           *
R/G C   P   T   A/V T   A/T T   A   L   A   P   R   G   G   S
CGC TGT CCG ACT GCA ACC GCC ACC GCT TTA GCG CCC CGG GGC GGA TCC
GGC TGT CCG ACC GTA ACT ATC ACC GCT TTA GCA CCC CGG GGA GGG TCC
*               *   *   *   *           *           *       *
R/G V
AGA GTC TGA
GGA GTT TGA
*
```

FIG. 5B

```
consensus:                   RL   LL    GNHAAGILT  G
hcrt1:    LGVDAQPLPDCCRQKTCSCRLYELLHGAGNHAAGILTLG
hcrt2:              PGPPGLQGRLQRLLQANGNHAAGILTMG
SECRETIN: HSDGTFTSKLSRLRDSARLQRLLQGLV HSDGTFTSK
                    * ********  **  ** *
```

```
     GCTAGGAGACATTGCGGCGGCGGTGGCGGCGTTGGCAGCAGCTGCAGACATGCTGCTGCT
  1  ------------+---------+---------+---------+---------+---------+  60
     CGATCCTCTGTAACGCCGCCGCCACCGCCGCAACCGTCGTCGACGTCTGTACGACGACGA
                                                         M  L  L  L

CAAGAAACAGACGGAGGACATCAGCAGTGTCTATGAGATCCGGGAGAAGCTGGGCTCGGG
 61  ------------+---------+---------+---------+---------+---------+ 120
     GTTCTTTGTCTGCCTCCTGTAGTCGTCACAGATACTCTAGGCCCTCTTCGACCCGAGCCC
     K  K  Q  T  E  D  I  S  S  V  Y  E  I  R  E  K  L  G  S  G

TGCCTTCTCTGAGGTGATGCTGGCCCAGGAAAGGGGCTCTGCTCATCTTGTGGCCCTCAA
121  ------------+---------+---------+---------+---------+---------+ 180
     ACGGAAGAGACTCCACTACGACCGGGTCCTTTCCCCGAGACGAGTAGAACACCGGGAGTT
     A  F  S  E  V  M  L  A  Q  E  R  G  S  A  H  L  V  A  L  K

GTGCATTCCCAAGAAAGCACTTCGGGGCAAGGAGGCCCTGGTGGAGAATGAGATCGCAGT
181  ------------+---------+---------+---------+---------+---------+ 240
     CACGTAAGGGTTCTTTCGTGAAGCCCCGTTCCTCCGGGACCACCTCTTACTCTAGCGTCA
     C  I  P  K  K  A  L  R  G  K  E  A  L  V  E  N  E  I  A  V

ACTCCGCAGGATTAGCCACCCCAACATTGTGGCTCTGGAGGACGTCCACGAGAGCCCTTC
241  ------------+---------+---------+---------+---------+---------+ 300
     TGAGGCGTCCTAATCGGTGGGGTTGTAACACCGAGACCTCCTGCAGGTGCTCTCGGGAAG
     L  R  R  I  S  H  P  N  I  V  A  L  E  D  V  H  E  S  P  S

CCATCTCTACTTGGCCATGGAGCTGGTAACAGGTGGTGAACTGTTTGACCGAATCATGGA
301  ------------+---------+---------+---------+---------+---------+ 360
     GGTAGAGATGAACCGGTACCTCGACCATTGTCCACCACTTGACAAACTGGCTTAGTACCT
     H  L  Y  L  A  M  E  L  V  T  G  G  E  L  F  D  R  I  M  E

GCGGGGCTCCTACACAGAGAAGGATGCGAGCCACCTTGTAGGGCAGGTCCTTGGTGCTGT
361  ------------+---------+---------+---------+---------+---------+ 420
     CGCCCCGAGGATGTGTCTCTTCCTACGCTCGGTGGAACATCCCGTCCAGGAACCACGACA
     R  G  S  Y  T  E  K  D  A  S  H  L  V  G  Q  V  L  G  A  V

CTCCTACCTTCATAGCCTGGGCATCGTGCACCGGGACCTCAAGCCTGAAAACCTCCTCTA
421  ------------+---------+---------+---------+---------+---------+ 480
     GAGGATGGAAGTATCGGACCCGTAGCACGTGGCCCTGGAGTTCGGACTTTTGGAGGAGAT
     S  Y  L  H  S  L  G  I  V  H  R  D  L  K  P  E  N  L  L  Y

TGCCACACCTTTTGAGGACTCCAAGATCATGGTCTCTGACTTTGGCCTGTCCAAAATTCA
481  ------------+---------+---------+---------+---------+---------+ 540
     ACGGTGTGGAAAACTCCTGAGGTTCTAGTACCAGAGACTGAAACCGGACAGGTTTTAAGT
     A  T  P  F  E  D  S  K  I  M  V  S  D  F  G  L  S  K  I  Q
```

FIG. 6A

```
        AGCTGGCAACATGCTAGGCACAGCCTGTGGGACCCCAGGATATGTGGCCCCAGAGCTCCT
541     ---------+---------+---------+---------+---------+---------+    600
        TCGACCGTTGTACGATCCGTGTCGGACACCCTGGGGTCCTATACACCGGGGTCTCGAGGA
         A  G  N  M  L  G  T  A  C  G  T  P  G  Y  V  A  P  E  L  L

GGAGCAGAAACCCTACGGGAAGGCCGTAGATGTGTGGGCCCTGGGTGTCATCTCCTACAT
601     ---------+---------+---------+---------+---------+---------+    660
        CCTCGTCTTTGGGATGCCCTTCCGGCATCTACACACCCGGGACCCACAGTAGAGGATGTA
         E  Q  K  P  Y  G  K  A  V  D  V  W  A  L  G  V  I  S  Y  I

CCTGCTGTGTGGGTACCCCCCCTTCTATGATGAGAGCGATCCTGAACTCTTCAGCCAGAT
661     ---------+---------+---------+---------+---------+---------+    720
        GGACGACACACCCATGGGGGGGAAGATACTACTCTCGCTAGGACTTGAGAAGTCGGTCTA
         L  L  C  G  Y  P  P  F  Y  D  E  S  D  P  E  L  F  S  Q  I

TCTGAGGGCCAGCTACGAGTTTGACTCTCCCTTTTGGGATGACATCTCAGAATCAGCCAA
721     ---------+---------+---------+---------+---------+---------+    780
        AGACTCCCGGTCGATGCTCAAACTGAGAGGGAAAACCCTACTGTAGAGTCTTAGTCGGTT
         L  R  A  S  Y  E  F  D  S  P  F  W  D  D  I  S  E  S  A  K

AGACTTCATTCGGCACCTTCTGGAACGTGATCCCCAGAAGAGGTTCACCTGCCAACAGGC
781     ---------+---------+---------+---------+---------+---------+    840
        TCTGAAGTAAGCCGTGGAAGACCTTGCACTAGGGGTCTTCTCCAAGTGGACGGTTGTCCG
         D  F  I  R  H  L  L  E  R  D  P  Q  K  R  F  T  C  Q  Q  A

CTTACAGCATCTCTGGATCTCTGGGGATGCAGCCTTGGACAGGGACATCCTAGGTTCTGT
841     ---------+---------+---------+---------+---------+---------+    900
        GAATGTCGTAGAGACCTAGAGACCCCTACGTCGGAACCTGTCCCTGTAGGATCCAAGACA
         L  Q  H  L  W  I  S  G  D  A  A  L  D  R  D  I  L  G  S  V

CAGTGAGCAGATCCAGAAGAATTTTGCCAGGACCCACTGGAAGCGTGCATTCAATGCCAC
901     ---------+---------+---------+---------+---------+---------+    960
        GTCACTCGTCTAGGTCTTCTTAAAACGGTCCTGGGTGACCTTCGCACGTAAGTTACGGTG
         S  E  Q  I  Q  K  N  F  A  R  T  H  W  K  R  A  F  N  A  T

ATCATTCCTACGTCACATCCGTAAGCTGGGACAGAGCCCAGAGGGTGAGGAGGCCTCCAG
961     ---------+---------+---------+---------+---------+---------+    1020
        TAGTAAGGATGCAGTGTAGGCATTCGACCCTGTCTCGGGTCTCCCACTCCTCCGGAGGTC
         S  F  L  R  H  I  R  K  L  G  Q  S  P  E  G  E  E  A  S  R

GCAGGGTATGACCCGTCACAGCCACCCAGGCCTTGGGACTAGCCAGTCTCCCAAGTGGTG
1021    ---------+---------+---------+---------+---------+---------+    1080
        CGTCCCATACTGGGCAGTGTCGGTGGGTCCGGAACCCTGATCGGTCAGAGGGTTCACCAC
         Q  G  M  T  R  H  S  H  P  G  L  G  T  S  Q  S  P  K  W  V
```

FIG. 6B

```
            ACAACCAGGTGGATGCCAAGGAAGGCCAAGTGGACTGACTCCTAGCTTTTCTTTCCTCCA
1081        ---------+---------+---------+---------+---------+---------+    1140
            TGTTGGTCCACCTACGGTTCCTTCCGGTTCACCTGACTGAGGATCGAAAAGAAAGGAGGT
             T  T  R  W  M  P  R  K  A  K  W  T  D  S

GCCCTTTTGATCTCCTTCCCTGATCCTTGTCCCCCGGACTGGCCTCTGTTGGAAAGTCCA
1141        ---------+---------+---------+---------+---------+---------+    1200
            CGGGAAAACTAGAGGAAGGGACTAGGAACAGGGGGCCTGACCGGAGACAACCTTTCAGGT

AGACCGTGGGTGTGATGCATGGCACTGGGGTATGGGGCTTCCCAAGTATGTCCCCAGCCT
1201        ---------+---------+---------+---------+---------+---------+    1260
            TCTGGCACCCACACTACGTACCGTGACCCCATACCCCGAAGGGTTCATACAGGGGTCGGA

CTGTCCTTTGTTGCTGCCACCCTCTATGGAAACTGAGGAGGTATTCAAAAATGGATTTGG
1261        ---------+---------+---------+---------+---------+---------+    1320
            GACAGGAAACAACGACGGTGGGAGATACCTTTGACTCCTCCATAAGTTTTTACCTAAACC

GGGCCATCCTTCCTGCACCTTGCACGCACATATGCATTGCGTGGCTGTTCTGTGCTTTGC
1321        ---------+---------+---------+---------+---------+---------+    1380
            CCCGGTAGGAAGGACGTGGAACGTGCGTGTATACGTAACGCACCGACAAGACACGAAACG

TGACTGTGGGTGGTCCTGCTTGTGTTGTAGCCCTTTAGTTCCTCCTCTTTCCAACCAATA
1381        ---------+---------+---------+---------+---------+---------+    1440
            ACTGACACCCACCAGGACGAACACAACATCGGGAAATCAAGGAGGAGAAAGGTTGGTTAT

AAGACAAACAGAACAATG
1441        ---------+--------  1458
            TTCTGTTTGTCTTGTTAC
```

HYPOTHALAMUS-SPECIFIC POLYPEPTIDES

REFERENCE TO RELATED APPLICATION

This application claims the benefit of U.S. Provisional Application Ser. No. 60/023,220, filed Aug. 2, 1996, which is explicitly incorporated by reference, as are all references cited herein.

GOVERNMENTAL RIGHTS

This invention was made with governmental support from the United States Government, National Institutes of Health, Grants GM32355 and NS33396; the United States Government has certain rights in the invention.

FIELD OF THE INVENTION

This invention relates to the identification, isolation, sequencing, use, and expression of hypothalamus-specific proteins and fragments thereof.

BACKGROUND OF THE INVENTION

The hypothalamus, a phylogenetically ancient region of the mammalian brain, is responsible for the integration of the central nervous system and the endocrine system and is particularly related to the physiological response to stress. In contrast to laminar cortical structures such as the cerebellum and hippocampus whose final functions rely on innervation from the thalamus and brain stem, the hypothalamus is organized as a collection of distinct, autonomously active nuclei with discrete functions. Ablation and electrical stimulation studies and medical malfunctions have implicated several of these nuclei as central regulatory centers for major autonomic and endocrine homeostatic systems mediating processes such as reproduction, lactation, fluid balance, metabolism, and aspects of behaviors, such as circadian rhythmicity, basic emotions, feeding and drinking, mating activities, and responses to stress, as well as normal development of the immune system (Shepherd, G. M., Neurobiology, 3rd ed. Oxford University Press, New York, 1994). Distinct hormones and releasing factors have been associated with some of these nuclei but, at best, the organizations and molecular operations of these structures are only partially understood.

A substantial portion of a mammal's genetic endowment is dedicated to the function of its central nervous system, as evidenced by the substantial number of mRNAs selectively expressed in the brain (Sutcliffe, J. G., Ann. Rev. Neurosci. 11:157–198, 1988). Many of these have been observed to be selectively associated with distinct neural subsets. Existing knowledge of the expression of specific hypothalamic hormones and releasing factors suggests that ensembles of mRNAs selectively associated with discrete hypothalamic nuclei may encode proteins singularly associated with the unique functions of those nuclei.

SUMMARY OF THE INVENTION

The present invention provides peptides and polypeptides found in the hypothalamus region of the mammalian brain. Preferably, the peptides and polypeptides are enriched in the hypothalamus relative to other regions of the brain. More preferably the peptides and polypeptides are specific to the hypothalamus. One embodiment is the rat polypeptide hypocretin also referred to as, H35 protein or clone 35 protein (SEQ ID NO:1) and polypeptide analogs thereof having at least one conservative amino acid substitution. Another embodiment is the mouse hypocretin polypeptide (SEQ ID NO:2) and polypeptide analogs thereof having at least one conservative amino acid substitution.

The present invention also provides polynucleotides encoding peptides and polypeptides found in the hypothalamus region of the brain. Preferably, the polynucleotides encoding peptides and polypeptides are enriched in the hypothalamus relative to other regions of the brain. More preferably the polynucleotides encoding peptides and polypeptides are specific to the hypothalamus. One embodiment is a polynucleotide chosen from the group consisting of the polynucleotide of SEQ ID NO:3, a polynucleotide having at least about 95% of its nucleotide sequence identical to the polynucleotide of SEQ ID NO:3, and polynucleotides hybridizing to the polynucleotide of SEQ ID NO: 3. Another embodiment is a polynucleotide chosen from the group consisting of the polynucleotide of SEQ ID NO:4, a polynucleotide having at least about 95% of its nucleotide sequence identical to the polynucleotide of SEQ ID NO:4, and polynucleotides hybridizing to the polynucleotide of SEQ ID NO: 4.

Also provided are vectors for the expression of the novel polynucleotides operably linked to control sequences capable of directing the production of the novel polypeptides in suitable host cells.

In other aspects this invention provides pharmaceutical compositions of the polynucleotides, polypeptides and peptides, antibodies to the peptides and polypeptides as well as compositions thereof. This invention also provides assay methods and kits for practicing the methods, and methods for using the polynucleotides, peptides and polypeptides for diagnostic and therapeutic purposes.

BRIEF DESCRIPTION OF THE DRAWINGS

In the Drawings,

FIGS. 1A–1C shows the results of subtractive screening, enriched for sequences selectively expressed in hypothalamus. Replicate dot blots on which the indicated masses of plasmid DNA for clones of neuron-specific enolase (NSE), cyclophilin, proopiomelanocortin (POMC), vasopressin, the vector pT7T3D, protein kinase Cδ (PKCδ) and growth hormone (GH) were manually spotted and hybridized with cDNA probes made from cRNA transcribed from the target or subtracted libraries, or an equal mixture of the cerebellum and hippocampus driver libraries. Comparison of the signal intensities for the vasopressin dilution series dots at several levels of autoradiographic exposure suggested a 20-to-30 fold increase in the specific activity of vasopressin cDNA.

FIGS. 3A–3D distribution of hypothalamic mRNAs. Northern blots with poly(A)+ RNA isolated from extracts of whole brain, olfactory bulb, cerebral cortex, hippocampus, hypothalamus, thalamus, cerebellum, pituitary, liver, kidney and heart were probed with cDNA inserts from the indicated clones. A cyclophilin probe was included in the series as a control for comparable blot loading and RNA integrity. The two hypothalamus samples represent inadvertent mixtures of approximately equal parts of hypothalamus and striatum. The expression patterns are grouped into four classes (A,B, C,D). Only the regions of the blots containing the hybridized signal are shown.

FIGS. 5A and 5B show a comparison of rat and mouse cDNA and amino acid sequences corresponding to clone 35 and the amino acid sequence of the peptide hormone secretin. A. The amino acid sequence is listed on the top line (rat SEQ ID NO: 1/mouse SEQ ID NO: 2), the rat nucleotide sequence (SEQ ID NO: 14) on the second line and the mouse nucleotide sequence (SEQ ID NO: 15) is listed on the third line. Differences in nucleotide sequences are indicated by asterisks below each different base, amino acid differences are indicated by alternatives (rat/mouse) listed above the encoding triplets. Tandem basic amino acids (putative sites for proteolytic maturation) are indicated in bold italics, as is the serine residue most likely to represent the end of the secretion signal. B. Alignment of hcrt1 and hcrt2 amino acid sequences (SEQ ID NO: 7 and SEQ ID NO: 9, respectively) with the amino acid sequence of secretin (SEQ ID NO: 21). The first 9 amino acid residues of secretin have been repeated to indicate apparent circular permutation. The identities between the hypocretins and members of the glucagon/vasoactive intestinal polypeptide/secretin family (H.-C.Fehmann, R. Goke, B. Goke, Endocrine Reviews, 16, 390 (1995)) are indicated by asterisks; the hcrt1 and hcrt2 consensus residues (RL LL GNHAAGILT G; SEQ ID NO: 20) appear above the alignment.

FIGS. 6A–6C show the cDNA (SEQ ID NO: 5) and amino acid sequence (SEQ ID NO: 29) of clone 29.

DETAILED DESCRIPTION OF PREFERRED EMBODIMENTS

Figure 2A:
FIGS. 2A–2D shows the results of cDNA library Southern blotting with clones representative of the four distribution classes. The electrophoretic lanes contain the cerebellum first driver library (D1), the hippocampus second driver library (D2), and the hypothalamus target library (T) cleaved with HaeIII and hybridized with the inserts from clone 35 (Panel A), clone 10 (Panel B), clone 86 (Panel C) and clone 19 (Panel D).
Figure 2B:
Figure 2C:
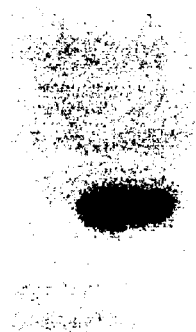
Figure 2D:

The following definitions are set forth to illustrate and define the meaning and scope of the various terms used to describe the invention herein. All patents and other publications mentioned in this specification are expressly incorporated by reference herein.

A. Definitions

Amino Acid Residue: An amino acid formed upon chemical digestion (hydrolysis) of a polypeptide at its peptide linkages. The amino acid residues described herein are preferably in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxy group present at the carboxy terminus of a polypeptide. The standard polypeptide nomenclature (described in *J. Biol. Chem.*, 243:3552–59 (1969) and adopted at 37 CFR §1.822(b)(2)) that provides one letter and three letter codes for amino acid residues is used.

It should be noted that all amino acid residue sequences represented herein by formulae have a left- to-right orientation in the conventional direction of amino terminus to carboxy terminus. In addition, the phrase "amino acid residue" is broadly defined to include modified and unusual amino acids, such as those listed in 37 CFR 1.822(b)(4), and incorporated herein by reference. Furthermore, it should be noted that a dash at the beginning or end of an amino acid residue sequence indicates a peptide bond to a further sequence of one or more amino acid residues or a covalent bond to an amino-terminal group such as $NH_2$ or acetyl or to a carboxy-terminal group such as COOH.

Recombinant DNA molecule: a DNA molecule produced by operatively linking two DNA segments. Thus, a recombinant DNA molecule is a hybrid DNA molecule comprising at least two nucleotide sequences not normally found together in nature.

Receptor: A receptor is a molecule, such as a protein, glycoprotein and the like, that can specifically (non-randomly) bind to another molecule.

Antibody: The term antibody in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab', and $F(ab')_2$.

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Monoclonal Antibody: A monoclonal antibody in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody.

Upstream: In the direction opposite to the direction of DNA transcription, and therefore going from 5' to 3' on the non-coding strand, or 3' to 5' on the mRNA.

Downstream: Further along a DNA sequence in the direction of sequence transcription or read out, that is traveling in a 3'- to 5'-direction along the non-coding strand of the DNA or 5'- to 3'-direction along the RNA transcript.

Polypeptide: A linear series of amino acid residues connected to one another by peptide bonds between the alpha-amino group and carboxy group of contiguous amino acid residues.

Protein: A linear series of more than 50 amino acid residues connected one to the other as in a polypeptide.

Substantially Purified or Isolated: When used in the context of polypeptides or proteins, the terms describe those molecules that have been separated from components that naturally accompany them. Typically, a monomeric protein is substantially pure when at least about 60% to 75% of a sample exhibits a single polypeptide backbone. Minor variants or chemical modifications typically share the same polypeptide sequence. A substantially purified protein will typically comprise over about 85% to 90% of a protein sample, more usually about 95%, and preferably will be over about 99% pure. Protein or polypeptide purity or homogeneity may be indicated by a number of means well known in the art, such as polyacrylamide gel electrophoresis of a sample, followed by visualization thereof by staining. For certain purposes, high resolution is needed and high performance liquid chromatography (HPLC) or a similar means for purification utilized.

Synthetic Peptide: A chemically produced chain of amino acid residues linked together by peptide bonds that is free of naturally occurring proteins and fragments thereof.

Nucleic acid or polynucleotide sequence: includes, but is not limited to, eucaryotic mRNA, cDNA, genomic DNA, and synthetic DNA and RNA sequences, comprising the natural nucleoside bases adenine, guanine, cytosine, thymidine, and uracil. The term also encompasses sequences having one or more other bases including, but not limited to 4-acetylcytosine, 8-hydroxy-N6-methyladenine, aziridinylcytosine, pseudoisocytosine, 5-(carboxyhydroxylmethyl)uracil, 5-fluorouracil, 5-bromouracil, 5-carboxymethylaminomethyl-2-thiouracil, 5-carboxymethylaminomethyluracil, dihydrouracil, inosine, N6-isopentenyl-adenine, 1-methyladenine, 1-methylpseudouracil, 1-methylguanine, 1-methyl-inosine, 2,2-dimethylguanine, 2-methyladenine, 2-methylguanine, 3-methyl-cytosine, 5-methylcytosine, N6-methyladenine, 7-methylguanine, 5-methyl-aminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, and 2,6-diaminopurine.

Coding sequence or open reading frame: a polynucleotide or nucleic acid sequence which is transcribed (in the case of DNA) or translated (in the case of mRNA) into a polypeptide in vitro or in vivo when placed under the control of appropriate regulatory sequences. The boundaries of the coding sequence are determined by a translation start codon at the 5' (amino) terminus and a translation stop codon at the 3' (carboxy) terminus. A transcription termination sequence will usually be located 3' to the coding sequence.

Nucleic acid control sequences: translational start and stop codons, promoter sequences, ribosome binding sites, polyadenylation signals, transcription termination sequences, upstream regulatory domains, enhancers, and the like, as are necessary and sufficient for the transcription and translation of a given coding sequence in a defined host cell. Examples of control sequences suitable for eucaryotic cells are promoters, polyadenylation signals, and enhancers. All of these control sequences need not be present in a recombinant vector so long as those necessary and sufficient for the transcription and translation of the desired gene are present.

Operably or operatively linked: the configuration of the coding and control sequences so as to perform the desired function. Thus, control sequences operably linked to a coding sequence are capable of effecting the expression of the coding sequence. A coding sequence is operably linked to or under the control of transcriptional regulatory regions in a cell when DNA polymerase will bind the promoter sequence and transcribe the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

Heterologous and exogenous: as they relate to nucleic acid sequences such as coding sequences and control sequences, denote sequences that are not normally associated with a region of a recombinant construct, and are not normally associated with a particular cell. Thus, a "heterologous" region of a nucleic acid construct is an identifiable segment of nucleic acid within or attached to another nucleic acid molecule that is not found in association with the other molecule in nature. For example, a heterologous region of a construct could include a coding sequence flanked by sequences not found in association with the coding sequence in nature. Another example of a heterologous coding sequence is a construct where the coding sequence itself is not found in nature (e.g., synthetic sequences having codons different from the native gene). Similarly, a host cell transformed with a construct which is not normally present in the host cell would be considered heterologous for purposes of this invention.

Expression system: polynucleotide sequences containing a desired coding sequence and control sequences in operable linkage, so that cells transformed with these sequences are capable of producing the encoded product. In order to effect transformation, the expression system may be included on a discrete vector; however, the relevant polynucleotide may also be integrated into the host chromosome.

Vector: a recombinant polynucleotide comprised of single strand, double strand, circular, or supercoiled DNA or RNA. A typical vector may be comprised of the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. One or more of these elements may be omitted in specific applications. The nucleic acid cassette can include a restriction site for insertion of the nucleic acid sequence to be expressed. In a functional vector the nucleic acid cassette contains the nucleic acid sequence to be expressed including translation initiation and termination sites. An intron optionally may be included in the construct, preferably $\geq 100$ bp and placed 5' to the coding sequence.

A vector is constructed so that the particular coding sequence is located in the vector with the appropriate regulatory sequences, the positioning and orientation of the coding sequence with respect to the control sequences being such that the coding sequence is transcribed under the "control" of the control sequences. Modification of the sequences encoding the particular protein of interest may be desirable to achieve this end. For example, in some cases it may be necessary to modify the sequence so that it may be attached to the control sequences with the appropriate orientation; or to maintain the reading frame. The control sequences and other regulatory sequences may be ligated to the coding sequence prior to insertion into a vector. Alternatively, the coding sequence can be cloned directly into an expression vector which already contains the control sequences and an appropriate restriction site which is in reading frame with and under regulatory control of the control sequences.

Suitable marker sequences for identification and isolation of correctly transfected cells include the thymidine kinase (tk), dihydrofolate reductase (DHFR), and aminoglycoside phosphotransferase (APH) genes. The latter imparts resistance to the aminoglycoside antibiotics, such as kanamycin, neomycin, and geneticin. These, and other marker genes such as those encoding chloramphenicol acetyltransferase (CAT) and β-galactosidase (β-gal), may be incorporated into the primary nucleic acid cassette along with the gene expressing the desired therapeutic protein, or the selection markers may be contained on separate vectors and cotransfected.

The term "biochemically equivalent variations" means protein or nucleic acid sequences which differ in some respect from the specific sequences disclosed herein, but nonetheless exhibit the same or substantially the same functionality. In the case of cDNA, for example, this means that modified sequences which contain other nucleic acids than those specifically disclosed are encompassed, provided that the alternate cDNA encodes mRNA which in turn encodes a protein of this invention. Such modifications may involve the substitution of only a few nucleic acids, or many. The modifications may involve substitution of degenerate coding sequences or replacement of one coding sequence with another; introduction of non-natural nucleic acids is included. Preferably, the modified nucleic acid sequence hybridizes to and is at least 95% complementary to the sequence of interest.

Similarly, in the case of the proteins and polypeptides of this invention, alterations in the amino acid sequence which do not affect functionality may be made. Such "biochemically equivalent muteins" may involve replacement of one amino acid with another, use of side chain modified or non-natural amino acids, and truncation. The skilled artisan will recognize which sites are most amenable to alteration without affecting the basic function.

The expression products described herein are proteins and polypeptides having a defined chemical sequence. However, the precise structure depends on a number of factors, particularly chemical modifications common to proteins. For example, since all proteins contain ionizable amino and carboxyl groups, the protein may be obtained in acidic or basic salt form, or in neutral form. The primary amino acid sequence may be derivatized using sugar molecules (glycosylation) or by other chemical derivatizations involving covalent or ionic attachment with, for example, lipids, phosphate, acetyl groups and the like, often occurring through association with saccharides. These modifications may occur in vitro, or in vivo, the latter being performed by a host cell through post-translational processing systems. Such modifications may increase or decrease the biological activity of the molecule, and such chemically modified molecules are also intended to come within the scope of the invention.

B. Hypocretin Proteins and Polypeptides

Hypocretin or clone H35, has been cloned in both rat and mouse. The amino acid residue sequence in these two mammalian species is not identical but is sufficiently similar to permit generalization regarding function, and so that one can identify and isolate the hypocretin gene in any mammalian species.

Variations at both the amino acid and nucleotide sequence level are described in isolates of hypocretin, and such variations are not to be construed as limiting. For example, allelic variation within a mammalian species can tolerate a several percent difference between isolates of a type of hypocretin, which differences comprise non-deleterious variant amino acid residues. Thus a protein of about 95% homology, and preferably at least 98% homology, to a disclosed hypocretin is considered to be an allelic variant of the disclosed hypocretin, and therefore is considered to be a hypocretin of this invention.

As disclosed herein, hypocretin is produced first in vivo in precursor form, and is then processed into smaller polypeptides having biological activity as described herein. Insofar as these different polypeptide forms are useful, the term hypocretin protein or polypeptide connotes all species of polypeptide having an amino acid residue sequence derived from the hypocretin gene.

The complete coding nucleotide sequence, clone 35, of rat H35 cDNA is 569 nucleotides in length, and is listed in SEQ ID NO 3. The complete preprohypocretin cDNA clone presents a 390 nucleotide open reading frame (ORF) plus triplet termination codons (second line in FIG. 5 and SEQ ID NO. 14). There is a N-terminal signal peptide with a cleavage site between amino acid positions 27 and 28, corresponding to a cleavage site after nucleotide position 172 of SEQ ID NO:3.

Translation of this rat cDNA sequence produces a novel protein of 130 amino acid residues, referred to as rat preprohypocretin. The amino acid sequence of rat preprohypocretin is listed in SEQ ID NO: 1. The amino acid sequence of mouse preprohypocretin is listed in SEQ ID NO: 2.

A hypocretin protein of this invention can be in a variety of forms, depending upon the use therefor, as described herein. For example, a hypocretin can be isolated from a natural tissue.

Alternatively, a hypocretin protein of this invention can be a recombinant protein, that is, produced by recombinant DNA methods as described herein. A recombinant hypocretin protein need not necessarily be substantially pure, or even isolated, to be useful in certain embodiments, although recombinant production methods are a preferred means to produce a source for further purification to yield an isolated or substantially pure receptor composition. A recombinant hypocretin protein can be present in or on a mammalian cell line or in crude extracts of a mammalian cell line.

In one embodiment, a hypocretin protein is substantially free of other neuropeptides, so that the purity of a hypocretin reagent, and thus freedom from pharmacologically distinct proteins, facilitates use in the screening methods. The recombinant production methods are ideally suited to produce significantly improved purity in this regard, although biochemical purification methods from natural sources are also included. In this regard, a hypocretin protein is substantially free from other neuropeptides if there are insufficient other neuropeptides such that pharmacological cross-reactivity is not detected in conventional screening assays for ligand binding or biological activity. Alternatively, recombinant hypocretin fusion proteins can be produced by joining nucleotides encoding additional amino acid residue sequence in proper reading frame at the 3' end of the hypocretin sequence. The fusion protein thus produced exhibits properties of the added amino acid sequence in addition to the properties of hypocretin. For example, the additional amino acid sequence may serve to help identify and purity the recombinantly produced hypocretin fusion protein. One preferred hypocretin fusion protein is hypocretin-poly(His).

Preferably, a hypocretin protein of this invention is present in a composition in an isolated form, i.e., comprising at least about 0.1 percent by weight of the total composition, preferably at least 1%, and more preferably at least about 90%. Particularly preferred is a substantially pure preparation of hypocretin, that is at least 90% by weight, and more preferably at least 99% by weight. Biochemical methods useful for the enrichment and preparation of an isolated hypocretin based on the chemical properties of a polypeptide are well known, and can be routinely used for the production of proteins which are enriched by greater than 99% by weight.

An isolated or recombinant hypocretin protein of this invention can be used for a variety of purposes, as described further herein. A hypocretin protein can be used as an immunogen to produce antibodies immunoreactive with hypocretin. Hypocretin proteins can be used in in vitro ligand binding assays for identifying ligand binding specificities, and agonists or antagonists thereto, to characterize candidate pharmaceutical compounds useful for modulating hypocretin function, and as therapeutic agents for effecting hypocretin functions. Other uses will be readily apparent to one skilled in the art.

Furthermore, the invention includes analogs of a hypocretin protein of this invention. An analog is a man-made variant which exhibits the qualities of a hypocretin of this invention in terms of immunological reactivity, ligand binding capacity or the like functional properties of a hypocretin protein of this invention. An analog can therefore be a cleavage product of hypocretin, can be a polypeptide corresponding to a portion of hypocretin, can be hypocretin polypeptide in which a membrane anchor has been removed, and can be a variant hypocretin sequence in which some amino acid residues have been altered, to name a few alternatives.

Insofar as the present disclosure identifies hypocretin from different mammalian species, the present invention is not to be limited to a hypocretin protein derived from one or a few mammalian species. Thus, the invention includes a mammalian hypocretin protein, which can be derived, by recombinant DNA or biochemical purification from natural sources, from any of a variety of species including man, mouse, rabbit, rat, dog, cat, sheep, cow, and the like mammalian species, without limitation. Human and agriculturally relevant animal species are particularly preferred.

Exemplary hypocretin species identified herein are rat and mouse hypocretin.

The amino acid reside sequence of rat preprohypocretin is shown in SEQ ID NO 1, and corresponding nucleotide (cDNA) of rat preprohypocretin is shown in SEQ ID NO 3.

The amino acid residue sequence of mouse preprohypocretin is shown in SEQ ID NO 2, and corresponding nucleotide (cDNA) of mouse preprohypocretin is shown in SEQ ID NO 4.

A hypocretin protein of this invention can be prepared by a variety of means, although expression in a mammalian cell using a recombinant DNA expression vector is preferred. Exemplary production methods for a recombinant hypocretin are described in the Examples.

The invention also provides a method for the production of isolated hypocretin proteins, either as intact hypocretin protein, as fusion proteins or as smaller polypeptide fragments of hypocretin. The production method generally involves inducing cells to express a hypocretin protein of this invention, recovering the hypocretin from the resulting cells, and purifying the hypocretin so recovered by biochemical fractionation methods, using a specific antibody of this invention, or other chemical procedures.

The inducing step can comprise inserting a recombinant DNA vector encoding a hypocretin protein, or fragment thereof, of this invention, which recombinant DNA is capable of expressing a hypocretin, into a suitable host cell, and expressing the vector's hypocretin gene.

As used herein, the phrase "hypocretin polypeptide" refers to a polypeptide having an amino acid residue sequence that comprises an amino acid residue sequence that corresponds, and preferably is identical, to a portion of a hypocretin of this invention.

A hypocretin polypeptide of this invention is characterized by its ability to immunologically mimic an epitope (antigenic determinant) expressed by a hypocretin of this invention. Such a polypeptide is useful herein as a component in an inoculum for producing antibodies that immunoreact with native hypocretin and as an antigen in immunologic methods. Representative and preferred hypocretin polypeptides for use as an immunogen in an inoculum are shown herein.

As used herein, the phrase "immunologically mimic" in its various grammatical forms refers to the ability of a hypocretin polypeptide of this invention to immunoreact with an antibody of the present invention that recognizes a conserved native epitope of a hypocretin as defined herein.

It should be understood that a subject polypeptide need not be identical to the amino acid residue sequence of a hypocretin receptor, so long as it includes the required sequence.

In addition, certain hypocretin polypeptides derived from receptor binding portions of hypocretin have the capacity to inhibit the binding of the hypocretin that would normally bind a hypocretin receptor. Thus, the invention also includes hypocretin polypeptides which are specifically designed for their capacity to mimic exposed regions of hypocretin involved in hypocretin receptor binding interactions and thereby receptor function. Therefore, these polypeptides have the capacity to function as analogs to hypocretin, and thereby block function.

In addition, polypeptides corresponding to exposed domains have the ability to induce antibody molecules that immunoreact with a hypocretin of this invention at portions of hypocretin involved in receptor protein function, and therefor the antibodies are also useful at modulating normal hypocretin function.

A hypocretin polypeptide is preferably no more than about 120 amino acid residues in length for reasons of ease of synthesis. Thus, it more preferred that a hypocretin polypeptide be no more that about 100 amino acid residues, still more preferably no more than about 50 residues, and optimally less than 40 amino acid residues in length when synthetic methods of production are used. Exemplary polypeptides are hcrt1 and hcrt2.

The present invention also includes a hypocretin polypeptide that has an amino acid residue sequence that corresponds to the sequence of the hypocretin protein shown in the sequence listings, and includes an amino acid residue sequence represented by a formula selected from the group consisting of the polypeptides shown in the sequence listings. In this embodiment, the polypeptide is further characterized as having the ability to mimic a hypocretin epitope and thereby inhibits hypocretin function in a classic hypocretin receptor activation assay, as described herein.

Due to the three dimensional structure of a native folded hypocretin molecule, the present invention includes that multiple regions of hypocretin are involved in hypocretin receptor function, which multiple and various regions are defined by the various hypocretin polypeptides described above. A preferred hypocretin receptor ligand is hcrt. The ability of the above-described polypeptides to inhibit receptor-ligand binding can readily be measured in a ligand binding assay as is shown in the Examples herein. Similarly, the ability of the above-described polypeptides to inhibit hypocretin receptor function can readily be measured in a receptor assay as is described herein.

In another embodiment, the invention includes hypocretin polypeptide compositions that comprise one or more of the different hypocretin polypeptides described above which inhibit hypocretin receptor function, admixed in combinations to provide simultaneous inhibition of multiple contact sites on the hypocretin receptor.

A subject polypeptide includes any analog, fragment or chemical derivative of a polypeptide whose amino acid residue sequence is shown herein so long as the polypeptide is capable of mimicking an epitope of hypocretin. Therefore, a present polypeptide can be subject to various changes, substitutions, insertions, and deletions where such changes provide for certain advantages in its use. In this regard, a hypocretin polypeptide of this invention corresponds to, rather than is identical to, the sequence of a hypocretin protein where one or more changes are made and it retains the ability to induce antibodies that immunoreact with a hypocretin of this invention.

The term "analog" includes any polypeptide having an amino acid residue sequence substantially identical to a sequence specifically shown herein in which one or more residues have been conservatively substituted with a functionally similar residue and which displays the ability to induce antibody production as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and omithine may be substituted for lysine. D-amino acids may also be included in place of one or more L-amino acids. Polypeptides of the present invention also include any polypeptide having one or more additions and deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

When a polypeptide of the present invention has a sequence that is not identical to the sequence of a hypocretin polypeptide, it is typically because one or more conservative or non-conservative substitutions have been made, usually no more than about 30 number percent, more usually no more than 20 number percent, and preferably no more than 10 number percent of the amino acid residues are substituted. Additional residues may also be added at either terminus for the purpose of providing a "linker" by which the polypeptides of this invention can be conveniently affixed to a label or solid matrix, or carrier. Preferably the linker residues do not form a hypocretin epitope, i.e., are not similar is structure to a hypocretin protein.

Labels, solid matrices and carriers that can be used with the polypeptides of this invention are described hereinbelow.

Amino acid residue linkers are usually at least one residue and can be 40 or more residues, more often 1 to 10 residues, but do not form a hypocretin epitope. Typical amino acid residues used for linking are tyrosine, cysteine, lysine, glutamic and aspartic acid, or the like. In addition, a subject polypeptide can differ, unless otherwise specified, from the natural sequence of a hypocretin protein by the sequence being modified by terminal-$NH_2$ acylation, e.g., acetylation, or thioglycolic acid amidation, by terminal-carboxlyamidation, e.g., with ammonia, methylamine, and the like.

When coupled to a carrier to form what is known in the art as a carrier-hapten conjugate, a hypocretin polypeptide of the present invention is capable of inducing antibodies that immunoreact with hypocretin. In view of the well established principle of immunologic cross-reactivity, the present invention therefore includes antigenically related variants of the polypeptides shown herein. An "antigenically related variant" is a subject polypeptide that is capable of inducing antibody molecules that immunoreact with a polypeptide described herein and with a hypocretin protein of this invention.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

A hypocretin polypeptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in J. M. Steward and J. D. Young, "Solid Phase Peptide Synthesis", W.H. Freeman Co., San Francisco, 1969; M. Bodansky, et al., "Peptide Synthesis", John Wiley & Sons, Second Edition, 1976 and J. Meienhofer, "Hormonal Proteins and Peptides", Vol. 2, p. 46, Academic Press (New York), 1983 for solid phase peptide synthesis, and E. Schroder and K. Kubke, "The Peptides", Vol. 1, Academic Press (New York), 1965 for classical solution synthesis, each of which is incorporated herein by reference. Additional peptide synthesis methods are described by Sutcliffe in U.S. Pat. Nos. 4,900,811 and 5,242,798, which are hereby incorporated by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final polypeptide.

A hypocretin polypeptide can be used, inter alia, in the diagnostic methods and systems of the present invention to detect a hypocretin receptor or hypocretin itself present in a body sample, or can be used to prepare an inoculum as described herein for the preparation of antibodies that immunoreact with conserved epitopes on hypocretin.

In addition, certain of the hypocretin polypeptides of this invention can be used in the therapeutic methods of the present invention to inhibit hypocretin function as described further herein.

C. Nucleic Acids and Polynucleotides

The DNA segments of the present invention are characterized as including a DNA sequence that encodes a hypocretin protein of this invention. That is, the DNA segments of the present invention are characterized by the presence of some or all of a hypocretin structural gene. Preferably the gene is present as an uninterrupted linear series of codons where each codon codes for an amino acid residue found in the hypocretin protein, i.e., a gene free of introns.

One preferred embodiment is a DNA segment that codes an amino acid residue sequence that defines a hypocretin protein as defined herein, and the DNA segment is capable of expressing a hypocretin protein of this invention. A preferred DNA segment codes for an amino acid residue sequence substantially the same as, and preferably consisting essentially of, an amino acid residue sequence shown in the sequence listing for a hypocretin protein, such as in SEQ ID NOs 1 and 2.

The amino acid residue sequence of a protein or polypeptide is directly related via the genetic code to the deoxyribonucleic acid (DNA) sequence of the structural gene that codes for the protein. Thus, a structural gene or DNA segment can be defined in terms of the amino acid residue sequence, i.e., protein or polypeptide, for which it codes.

An important and well known feature of the genetic code is its degeneracy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

A nucleic acid is any polynucleotide or nucleic acid fragment, whether it be a polyribonucleotide of polydeoxyribonucleotide, i.e., RNA or DNA, or analogs thereof. In preferred embodiments, a nucleic acid molecule is in the form of a segment of duplex DNA, i.e, a DNA segment, although for certain molecular biological methodologies, single-stranded DNA or RNA is preferred.

DNA segments (i.e., synthetic oligonucleotides) that encode portions of hypocretin proteins can easily be synthesized by chemical techniques, for example, the phosphotriester method of Matteucci, et al., (*J. Am. Chem. Soc.*, 103:3185–3191, 1981) or using automated synthesis methods. In addition, larger DNA segments can readily be prepared by well known methods, such as synthesis of a group of oligonucleotides that define the DNA segment, followed by hybridization and ligation of oligonucleotides to build the complete segment.

Of course, by chemically synthesizing the coding sequence, any desired modifications can be made simply by substituting the appropriate bases for those encoding the native amino acid residue sequence.

Furthermore, DNA segments consisting essentially of structural genes encoding a hypocretin protein can be obtained from recombinant DNA molecules containing a gene that defines a hypocretin protein of this invention, and can be subsequently modified, as by site directed mutagenesis, to introduce any desired substitutions.

1. Cloning Hypocretin Genes

Hypocretin genes of this invention can be cloned by a variety of cloning methods and from any mammalian species. The cloning is based on the observation that there is a significant degree of homology between mammalian species for any given hypocretin of this invention, and therefor can be conducted according to the general methods described in the Examples, using nucleic acid homology strategies.

A typical degree of homology required to successfully clone a hypocretin is at least about 80% homologous at the DNA level, and at least about 90% homologous at the protein level. Preferred cloning strategies for isolating a nucleic acid molecule that encodes a hypocretin molecule of this invention are described in the Examples, and includes the recitation of polynucleotide probes useful for the screening of libraries of nucleic acid molecules believed to contain a target hypocretin gene.

Sources of libraries for cloning a hypocretin gene of this invention can include genomic DNA or messenger RNA (mRNA) in the form of a cDNA library from a tissue believed to express a hypocretin of this invention. Preferred tissues are brain tissues, particularly hypothalamic tissue. The similarities between rat and mouse hypocretin are further extended to the identification of a sequence of iteration of trinucleotide CTG repeats. For both mammals, a sequence of four iterations of the trinucleotide CTG repeats followed by two pairs of CTG are present encoding leucine residues. Thus, the presence of the iterations is typically located within the coding region for the signal peptide.

Such a triplet expansion in other genes has been implicated as causal in neurological diseases, e.g., myotonic dystrophy as described by Brook et al., *Cell*, 68:799–808 (1992) and fragile-X syndrome as described by Fu et al., *Cell*, 67:1047–1058 (1991). In myotonic dystrophy patients who are mildly affected, at least 50 CTG repeats are present. In severely affected individuals, the expansion can exist up to several kilobase pairs. In contrast, in the normal population, the repeat sequence is highly variable ranging from 5 to 27 copies. Individuals with varying severities of fragile-X have been similarly characterized.

Screening for the presence of a region of DNA in which the repeats are present in either normal, underexpansion or overexpansion form can provide a genetic basis for diagnosis for some diseases. The same may be true for hypocretin in that expansion of the region may contribute to the basis for a neuronal disorder or disease of the brain or other tissue.

2. Oligonucleotides

The invention also includes oligonucleotides useful for methods to detect the presence of a hypocretin gene or gene transcript (mRNA) in a tissue by diagnostic detection methods based on the specificity of nucleic acid hybridization or primer extension reactions. One embodiment includes any polynucleotide probe having a sequence of a portion of a hypocretin gene of this invention, or a related and specific sequence. Hybridization probes can be of a variety of lengths from about 10 to 5000 nucleotides long, although they will typically be about 20 to 500 nucleotides in length. Hybridization methods are extremely well known in the art and will not be described further here.

In a related embodiment, detection of hypocretin genes can be conducted by primer extension reactions such as the polymerase chain reaction (PCR). To that end, PCR primers are utilized in pairs, as is well known, based on the nucleotide sequence of the gene to be detected. Particularly preferred PCR primers can be derived from any portion of a hypocretin DNA sequence, but are preferentially from regions which are not conserved in other cellular proteins.

A preferred PCR primer pair useful for detecting hypocretin genes and hypocretin gene expression are described in the Examples. Nucleotide primers from the corresponding region of hypocretin described herein are readily prepared and used as PCR primers for detection of the presence or expression of the corresponding gene in any of a variety of tissues.

3. Expression Vectors

In addition, the invention includes a recombinant DNA molecule (recombinant DNA) containing a DNA segment of this invention encoding a hypocretin protein as described herein. A recombinant DNA can be produced by operatively linking a vector to a DNA segment of the present invention.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector of the present invention is at least capable of directing the replication, and preferably also expression, of a hypocretin structural gene included in DNA segments to which it is operatively linked.

In one embodiment, a vector of the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of a hypocretin gene in a bacterial host cell, such as *E. coli*, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmids are pUC8, pUC9, pBR322 and pBR329 available from Biorad Laboratories, (Richmond, Calif.), pRSET available from Invitrogen (San Diego, Calif.) and pPL and pKK223 available from Pharmacia, Piscataway, N.J.

Expression vectors compatible with eucaryotic cells, preferably those compatible with vertebrate cells, can also be used to form the recombinant DNA molecules of the present invention. Eucaryotic cell expression vectors are well known in the art and are available from several commercial sources. Typically, such vectors are provided containing convenient restriction sites for insertion of the desired DNA segment. Typical of such vectors are pSVL and pKSV-10 (Pharmacia), pBPV-1/pML2d (International Biotechnologies, Inc.), pTDT1 (ATCC, #31255), pRc/CMV (Invitrogen, Inc.), the vector pCMV4 described herein, and the like eucaryotic expression vectors.

In preferred embodiments, the eucaryotic cell expression vectors used to construct the recombinant DNA molecules of the present invention include a selection marker that is effective in an eucaryotic cell, preferably a drug resistance selection marker. A preferred drug resistance marker is the gene whose expression results in neomycin resistance, i.e., the neomycin phosphotransferase (neo) gene. Southern et al., *J. Mol. Appl. Genet.*, 1:327–341 (1982). Alternatively, the selectable marker can be present on a separate plasmid, and the two vectors are introduced by co-transfection of the host cell, and selected by culturing in the appropriate drug for the selectable marker.

4. Inhibitory Nucleic Acids

In accordance with one embodiment of the invention, nucleic acid molecules can be used in methodologies for the inhibition of hypocretin gene expression, thereby inhibiting the function of the hypocretin:hypocretin receptor binding interaction by blocking hypocretin expression.

To that end, the invention includes isolated nucleic acid molecules, preferably single-stranded nucleic acid molecules (oligonucleotides), having a sequence complementary to a portion of a structural gene encoding a hypocretin protein of this invention. Nucleic acid-based inhibition is well known and generally referred to as "anti-sense" technology by virtue of the use of nucleotide sequences having complementarily which can hybridize to the "sense" strand or mRNA, and thereby perturb gene expression. Typical oligonucleotides for this purpose are about 10 to 5,000, preferably about 20–1000, nucleotides in length and have a sequence capable of hybridizing specifically with a structural protein region of the nucleotide sequence that encodes a hypocretin protein of this invention.

In one embodiment, the invention includes repetitive units of the nucleotide sequence complementary to a portion of a hypocretin structural gene so as to present multiple sites for complementary binding to the structural gene. This feature may be provided in a single nucleic acid segment having repeating sequences defining multiple portions of a structural gene, by physical conjugation of DNA segments each containing a single portion of a structural gene, or a combination thereof comprising conjugates of DNA segments, each having one or more sequences complementary to a structural gene.

Nucleotide base modifications can be made to provide certain advantages to a DNA segments of this invention, referred to as nucleotide analogs. A nucleotide analog refers to moieties which function similarly to nucleotide sequences in a nucleic acid molecule of this invention but which have non-naturally occurring portions. Thus, nucleotide analogs can have altered sugar moieties or inter-sugar linkages. Exemplary are the phosphorothioate and other sulfur-containing species, analogs having altered base units, or other modifications consistent with the spirit of this invention.

Preferred modifications include, but are not limited to, the ethyl or methyl phosphorate modifications disclosed in U.S. Pat. No. 4,469,863 and the phosphorothioate modified deoxyribonucleotides described by LaPlanche et al., Nucl. Acids Res., 14:9081, 1986; and Stec et al., J. Am. Chem. Soc., 106:6077, 1984. These modifications provide resistance to nucleolytic degradation, thereby contributing to the increased half-life in therapeutic modalities. Preferred modifications are the modifications of the 3'-terminus using phosphothioate (PS) sulfurization modification described by Stein et al., Nucl. Acids Res., 16:3209, 1988.

In accordance with the methods of this invention in certain preferred embodiments, at least some of the phosphodiester bonds of the nucleotide sequence can be substituted with a structure which functions to enhance the ability of the compositions to penetrate into the region of cells where the hypocretin structural gene to be inhibited is located. It is preferred that such linkages be sulfur containing as discussed above, such as phosphorotioate bonds. Other substitutions can include alkyl phosphothioate bonds, N-alkyl phosphoramidates, phosphorodithioates, alkyl phosphonates, and short chain alkyl or cycloalkyl structures. In accordance with other preferred embodiments, the phosphodiester bonds are substituted with structures which are, at once, substantially non-ionic and non-chiral.

D. Anti-Hypocretin Antibodies

An antibody of the present invention, i.e., an anti-hypocretin antibody, in one embodiment is characterized as comprising antibody molecules that immunoreact with a hypocretin protein of this invention. Preferably, an antibody further immunoreacts with a hypocretin protein in situ, i.e., in a tissue section.

The invention describes an anti-hypocretin antibody that immunoreacts with any of the hypocretin polypeptides of this invention, preferably also immunoreacts with the corresponding recombinant hypocretin protein, and more preferably also reacts with a native protein in situ in a tissue section. Preferably, the antibody is substantially free from immunoreaction with other proteins or neuropeptides other than hypocretin. Assays for immunoreaction useful for assessing immunoreactivity are described herein.

In one embodiment, antibody molecules are described that immunoreact with a hypocretin receptor polypeptide of the present invention and that have the capacity to immunoreact with an exposed site on hypocretin that is required for hypocretin receptor binding. Thus, preferred antibody molecules in this embodiment also inhibit hypocretin receptor function, and are therefore useful therapeutically to block the receptor's function.

Exemplary hypocretin inhibitory antibodies immunoreact with a hypocretin polypeptide described herein that defines an exposed region of a hypocretin protein that is involved in hypocretin receptor function, such as ligand binding.

An antibody of the present invention is typically produced by immunizing a mammal with an inoculum containing a hypocretin polypeptide of this invention and thereby induce in the mammal antibody molecules having immunospecificity for the immunizing polypeptide. The antibody molecules are then collected from the mammal and isolated to the extent desired by well known techniques such as, for example, by using DEAE Sephadex to obtain the IgG fraction. Exemplary antibody preparation methods using hypocretin polypeptides in the immunogen are described herein in the Examples.

The preparation of antibodies against polypeptide is well known in the art. See Staudt et al., J. Exp. Med., 157:687–704 (1983), or the teachings of Sutcliffe, J. G., as described in U.S. Pat. No. 4,900,811, the teachings of which are hereby incorporated by reference.

Briefly, to produce a hypocretin peptide antibody composition of this invention, a laboratory mammal is inoculated with an immunologically effective amount of a hypocretin polypeptide, typically as present in a vaccine of the present invention. The anti-hypocretin antibody molecules thereby induced are then collected from the mammal as an antiserum and those immunospecific for both a hypocretin polypeptide and the corresponding recombinant hypocretin protein are isolated to the extent desired by well known techniques such as, for example, by immunoaffinity chromatography. Alternatively, the antiserum may be used.

To enhance the specificity of the antibody, the antibodies are preferably purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

The word "inoculum" in its various grammatical forms is used herein to describe a composition containing a hypocretin polypeptide of this invention as an active ingredient used for the preparation of antibodies against a hypocretin polypeptide. When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide" and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used.

The techniques of polypeptide conjugation or coupling through activated functional groups presently known in the art are particularly applicable. See, for example, Aurameas, et al., *Scand. J. Immunol.*, Vol. 8, Suppl. 7:7–23 (1978) and U.S. Pat. No. 4,493,795, No. 3,791,932 and No. 3,839,153. In addition, a site-directed coupling reaction can be carried out so that any loss of activity due to polypeptide orientation after coupling can be minimized. See, for example, Rodwell et al., Biotech., 3:889–894 (1985), and U.S. Pat. No. 4,671,958.

Exemplary additional linking procedures include the use of Michael addition reaction products, di-aldehydes such as glutaraldehyde, Klipstein, et al., *J. Infect. Dis.*, 147:318–326 (1983) and the like, or the use of carbodiimide technology as in the use of a water-soluble carbodiimide to form amide links to the carrier. Alternatively, the heterobifunctional cross-linker SPDP (N-succinimidyl-3-(2-pyridyldithio) proprionate)) can be used to conjugate peptides, in which a carboxy-terminal cysteine has been introduced.

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly D-lysine:D-glutamic acid, and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen is well known in the art. Inocula typically contain polypeptide concentrations of about 10 micrograms ($\mu$g) to about 500 milligrams (mg) per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

The antibody so produced can be used, inter alia, in the diagnostic methods and systems of the present invention to detect hypocretin present in a sample such as a tissue section or body fluid sample. Anti-hypocretin antibodies that inhibit hypocretin function can also be used in vivo in therapeutic methods as described herein.

A preferred anti-hypocretin antibody is a monoclonal antibody. A preferred monoclonal antibody of this invention comprises antibody molecules that immunoreact with a hypocretin polypeptide of the present invention as described for the anti-hypocretin antibodies of this invention. More preferably, the monoclonal antibody also immunoreacts with recombinantly produced whole hypocretin protein.

A monoclonal antibody is typically composed of antibodies produced by clones of a single cell called a hybridoma that secretes (produces) only one kind of antibody molecule. The hybridoma cell is formed by fusing an antibody-producing cell and a myeloma or other self-perpetuating cell line. The preparation of such antibodies was first described by Kohler and Milstein, *Nature*, 256:495–497 (1975), the description of which is incorporated by reference. The hybridoma supernates so prepared can be screened for the presence of antibody molecules that immunoreact with a hypocretin polypeptide, or for inhibition of hypocretin binding to hypocretin receptor as described herein.

Briefly, to form the hybridoma from which the monoclonal antibody composition is produced, a myeloma or other self-perpetuating cell line is fused with lymphocytes obtained from the spleen of a mammal hyperimmunized with a hypocretin antigen, such as is present in a hypocretin polypeptide of this invention. The polypeptide-induced hybridoma technology is described by Niman et al., *Proc. Natl. Acad. Sci., USA*, 80:4949–4953 (1983), the description of which is incorporated herein by reference.

It is preferred that the myeloma cell line used to prepare a hybridoma be from the same species as the lymphocytes. Typically, a mouse of the strain 129 G1X$^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas producing a monoclonal antibody of this invention are identified using the enzyme linked immunosorbent assay (ELISA) described in the Examples.

A monoclonal antibody of the present invention can also be produced by initiating a monoclonal hybridoma culture comprising a nutrient medium containing a hybridoma that produces and secretes antibody molecules of the appropriate polypeptide specificity. The culture is maintained under conditions and for a time period sufficient for the hybridoma to secrete the antibody molecules into the medium. The antibody-containing medium is then collected. The antibody molecules can then be further isolated by well known techniques.

Media useful for the preparation of these compositions are both well known in the art and commercially available and include synthetic culture media, inbred mice and the like. An exemplary synthetic medium is Dulbecco's Minimal Essential Medium (DMEM; Dulbecco et al., *Virol.* 8:396 (1959)) supplemented with 4.5 gm/1 glucose, 20 mM glutamine, and 20% fetal calf serum. An exemplary inbred mouse strain is the Balb/c.

Other methods of producing a monoclonal antibody, a hybridoma cell, or a hybridoma cell culture are also well known. See, for example, the method of isolating monoclonal antibodies from an immunological repertoire as described by Sastry, et al., *Proc. Natl. Acad. Sci. USA*, 86:5728–5732 (1989); and Huse et al., *Science*, 246:1275–1281 (1989).

The monoclonal antibodies of this invention can be used in the same manner as disclosed herein for antibodies of the present invention.

For example, the monoclonal antibody can be used in the therapeutic, diagnostic or in vitro methods disclosed herein where immunoreaction with hypocretin is desired.

Also included in this invention is the hybridoma cell, and cultures containing a hybridoma cell that produce a monoclonal antibody of this invention.

E. Diagnostic Methods

The present invention includes various assay methods for determining the presence, and preferably amount, of hypocretin in a body sample such as a tissue sample, including tissue mass or tissue section, or in a biological fluid sample using a polypeptide, polyclonal antibody or monoclonal antibody of this invention as an immunochemical reagent to form an immunoreaction product whose amount relates, either directly or indirectly, to the amount of hypocretin in the sample.

Those skilled in the art will understand that there are numerous well known clinical diagnostic chemistry procedures in which an immunochemical reagent of this invention can be used to form an immunoreaction product whose amount relates to the amount of hypocretin in a body sample. Thus, while exemplary assay methods are described herein, the invention is not so limited.

For example, in view of the demonstrated property that hypocretin binds a hypocretin receptor, a hypocretin protein of this invention can be used directly as a probe for detection of a hypocretin receptor by binding thereto.

Additionally, one can use a nucleic acid molecule probes described herein to detect the presence in a cell or tissue of a hypocretin gene or expressed gene in the form of mRNA encoding a hypocretin protein of this invention, as described further herein. Suitable probe-based assays are described by Sutcliffe in U.S. Pat. Nos. 4,900,811 and 5,242,798, the disclosures of which are incorporated by reference.

Various heterogenous and homogeneous protocols, either competitive or noncompetitive, can be employed in performing an assay method of this invention.

For example, one embodiment includes a method for assaying the amount of hypocretin protein in a sample that utilizes an anti-hypocretin antibody to immunoreact with hypocretin protein in a sample. In this embodiment, the antibody immunoreacts with hypocretin to form a hypocretin-antibody immunoreaction complex, and the complex is detected indicating the presence of hypocretin in the sample.

An immunoassay method using an anti-hypocretin antibody molecule for assaying the amount of hypocretin in a sample typically comprises the steps of:

(a) Forming an immunoreaction admixture by admixing (contacting) a sample with an anti-hypocretin antibody of the present invention, preferably a monoclonal antibody. The sample is typically in the form of a fixed tissue section in a solid phase such that the immunoreaction admixture has both a liquid phase and a solid phase, and the antibody functions as a detection reagent for the presence of hypocretin in the sample.

Preferably, the sample is a brain tissue sample that has been prepared for immunohistological staining as is well known, although other tissue samples may be adsorbed onto a solid phase, including tissue extracts or body fluid. In that case the adsorption onto a solid phase can be conducted as described for well known Western blot procedures.

(b) The immunoreaction admixture is maintained under biological assay conditions for a predetermined time period such as about 10 minutes to about 16–20 hours at a temperature of about 4 degree Celsius to about 45 degree Celsius that, such time being sufficient for the hypocretin present in the sample to immunoreact with (immunologically bind) the antibody and form a hypocretin-containing immunoreaction product (immunocomplex).

Biological assay conditions are those that maintain the biological activity of the immunochemical reagents of this invention and the hypocretin sought to be assayed. Those conditions include a temperature range of about 4 degree Celsius to about 45 degree Celsius, a pH value range of about 5 to about 9 and an ionic strength varying from that of distilled water to that of about one molar sodium chloride. Methods for optimizing such conditions are well known in the art.

(c) The presence, and preferably amount, of hypocretin-containing immunoreaction product that formed in step (b) is determined (detected), thereby determining the amount of hypocretin present in the sample.

Determining the presence or amount of the immunoreaction product, either directly or indirectly, can be accomplished by assay techniques well known in the art, and typically depend on the type of indicating means used.

Preferably, the determining of step (c) comprises the steps of:

(i) admixing the hypocretin-containing immunoreaction product with a second antibody to form a second (detecting) immunoreaction admixture, said second antibody molecule having the capacity to immunoreact with the first antibody (primary) in the immunoreaction product.

Antibodies useful as the second antibody include polyclonal or monoclonal antibody preparations raised against the primary antibody.

(ii) maintaining said second immunoreaction admixture for a time period sufficient for said second antibody to complex with the immunoreaction product and form a second immunoreaction product, and (iii) determining the amount of second antibody present in the second immunoreaction product and thereby the amount of immunoreaction product formed in step (c).

In one embodiment, the second antibody is a labeled antibody (i.e., detecting antibody) such that the label provides an indicating means to detect the presence of the second immunoreaction product formed. The label is measured in the second immunoreaction product, thereby indicating the presence, and preferably amount, of second antibody in the solid phase.

Alternatively, the amount of second antibody can be determined by preparation of an additional reaction admixture having an indicating means that specifically reacts with (binds to) the second antibody, as is well known. Exemplary are third immunoreaction admixtures with a labeled anti-immunoglobulin antibody molecule specific for the second antibody. After third immunoreaction, the formed third immunoreaction product is detected through the presence of the label.

Exemplary methods involve the use of in situ immunoreaction methods using tissue sections, or Western blot procedures, as described by Sutcliffe in U.S. Pat. No. 4,900,811.

Another embodiment is a method for assaying the amount of therapeutically administered hypocretin protein or anti-hypocretin antibody in a body fluid sample such as cerebrospinal fluid (CSF), blood, plasma or serum. The method utilizes a competition reaction in which either a hypocretin polypeptide or an anti-hypocretin antibody molecule of this invention is present in the solid phase as an immobilized immunochemical reagent, and the other of the two reagents is present in solution in the liquid phase, in the form of a labeled reagent. A fluid sample is admixed thereto to form a competition immunoreaction admixture, and the resulting amount of label in the solid phase is proportional, either directly or indirectly, to the amount of hypocretin polypeptide or antibody in the fluid sample, depending upon the format.

One version of this embodiment comprises the steps of:

(a) Forming a competition immunoreaction admixture by admixing (contacting) a fluid sample with:

(1) an anti-hypocretin antibody according to this invention containing antibody molecules that immunoreact with a hypocretin protein of this invention, said antibody being operatively linked to a solid matrix such that the competition immunoreaction admixture has both a liquid phase and a solid phase, and (2) a polypeptide or recombinant hypocretin protein of the present invention that is immunoreactive with the added antibody. The admixed polypeptide/protein in the liquid phase (labeled competing antigen) is operatively linked to an indicating means as described herein.

(b) The competition immunoreaction admixture is then maintained for a time period sufficient for the competing antigen and the body sample antigen present in the liquid phase to compete for immunoreaction with the solid phase antibody. Such immunoreaction conditions are previously described, and result in the formation of an indicating means-containing immunoreaction product comprising the labeled competing antigen in the solid phase.

(c) The amount of indicating means present in the product formed in step (b) is then determined, thereby determining the presence, and preferably amount, of sample antigen present in the fluid sample.

Determining the indicating means in the solid phase is then conducted by the standard methods described herein.

A reverse version of this embodiment comprises the steps of:

(a) Forming a competition immunoreaction admixture by admixing a fluid sample with:

(1) an anti-hypocretin antibody according to the present invention; and (2) a hypocretin polypeptide or recombinant hypocretin protein of the present invention (capture antigen) that is immunoreactive with the antibody and is operatively linked to a solid matrix such that the competition immunoreaction admixture has both a liquid phase and a solid phase.

(b) The competition immunoreaction admixture is then maintained for a time period sufficient for any hypocretin antigen or anti-hypocretin antibody in the fluid to compete with the admixed antibody molecules for immunoreaction with the solid phase capture antigen and form an antibody-containing immunoreaction product in the solid phase.

(c) The amount of antibody present in the product formed in step (b) is then determined, thereby determining the presence and amount of target material in the fluid sample.

In preferred embodiments, the antibody is operatively linked to an indicating means such that the determining in step (c) comprises determining the amount of indicating means present in the product formed in step (b).

Preferably, the fluid sample is provided to a competition immunoreaction admixture as a known amount of CSF, blood, or a blood derived product such as serum or plasma. Further preferred are embodiments wherein the amount of immunochemical reagent in the liquid phase of the immunoreaction admixture is an excess amount relative to the amount of reagent in the solid phase. Typically, a parallel set of competition immunoreactions are established using a known amount of purified recombinant hypocretin or polypeptide in a dilution series so that a standard curve can be developed, as is well known. Thus, the amount of product formed in step (c) when using a fluid sample is compared to the standard curve, thereby determining the amount of target antigen present in the fluid.

In another embodiment, the method for assaying the amount of hypocretin in a sample utilizes a first capture antibody to capture and immobilize hypocretin in the solid phase and a second indicator antibody to indicate the presence of the captured hypocretin antigen. In this embodiment, one antibody immunoreacts with a hypocretin protein to form a hypocretin-antibody immunoreaction complex, and the other antibody is able to immunoreact with the hypocretin while present in the hypocretin-antibody immunoreaction complex. This embodiment can be practiced in two formats with the immobilized capture antibody being either of the two above-identified antibodies, and the indicator antibody being the other of the two antibodies.

Where an antibody is in the solid phase as a capture reagent, a preferred means for determining the amount of solid phase reaction product is by the use of a labeled hypocretin polypeptide, followed by the detection means described herein for other labeled products in the solid phase.

Also included are immunological assays capable of detecting the presence of immunoreaction product formation without the use of a label. Such methods employ a "detection means", which means are themselves well-known in clinical diagnostic chemistry and constitute a part of this invention only insofar as they are utilized with otherwise novel polypeptides, methods and systems. Exemplary detection means include methods known as biosensors and include biosensing methods based on detecting changes in the reflectivity of a surface, changes in the absorption of an evanescent wave by optical fibers or changes in the propagation of surface acoustical waves.

Alternative methods of expression, amplification, and purification will be apparent to the skilled artisan. Representative methods are disclosed in Sambrook, Fritsch, and Maniatis, eds. *Molecular Cloning, a Laboratory Manual*, 2nd Ed., Cold Spring Harbor Laboratory (1989) and in Ausabel et al., eds., *Current Protocols in Molecular Biology*, Wiley & Sons, Inc., New York (1989).

D. Specific Methods

Directional tag PCR subtractive hybridization was used to enrich a cDNA library for clones of mRNA species selectively expressed in the hypothalamus. Candidate clones identified by their hybridization to a subtracted hypothalamus probe were validated in three stages. First, a high throughput cDNA library Southern blot was used to demonstrate that the candidate corresponded to a species enriched in the subtracted library. Second, candidate clones positive in the first assay were used as probes for Northern blots with RNA from several brain regions and peripheral tissues. Finally, candidate clones that were still positive were subjected to in situ hybridization analysis to detect the hypothalamic regions that express the corresponding mRNAs.

Typically, subtractive hybridization protocols utilize a single target-driver dichotomy for enrichment of target-specific species. In the current study, a two-step subtraction protocol, first depleting hypothalamus sequences with a cerebellum driver, and then with a hippocampus driver, was employed. Previous studies using single step subtraction methodology had been successful in finding clones of species enriched in a target compared to the single driver tissue, only to find considerable expression in other brain regions. The present protocol was designed to provide a more stringent selection for clones of mRNAs with high selectivity for the target. Grids of the subtracted library were prepared and probed as described by Usui, H., Falk, J. D., Dopazo, A., de Lecea, L., Erlander, M. G., & Sutcliffe, J. G., *J. Neurosci*. 14:4915–4926 (1994). DNA sequence analysis, Northern blotting and in situ hybridization were performed as described by Usui et al., supra, and de Lecea, L., Soriano, E., Criado, J. R., Steffensen, S. C., Henriksen, S. J., & Sutcliffe, J. G., *Molec. Brain Res* 25:286–296 (1994).

In situ hybridization analysis was performed essentially as described by Gall, C. M. & Isackson, P. M., *Science* 245: 758–761 (1989) and by Erlander, M. G., et al., *Proc. Natl. Acad. Sci. USA* 90: 3452–3456 (1993). Coronal sections about 25 μm thick cut from brains of adult Sprague-Dawley rats were hybridized at 55 degrees Celsius for 16 hours with $^{35}$S-labelled single-stranded RNA probes at $10^7$ counts per minute per ml. Free-floating sections were treated with Rnase A at 4 μg/ml at 37 degrees Celsius for 1 hour and washed in 1×SSC (15 mM NaCl, 1.5 mM Na citrate), 50% formamide at 55 degrees Celsius for 2 hours. Final stringency washes were in 0.1×SSC at 68 degrees Celsius for 1 hour. Sections were mounted on coated slides, dehydrated and exposed to Kodak XAR film for 5 days at room temperature.

For cDNA library Southern blotting, 2 μg of each library was digested with HaeIII, separated by electrophoresis, transferred to nylon membranes, and hybridized to individual clones, as described in Usui et al, supra.

To recognize mRNAs that are selectively expressed in the hypothalamus, poly(A)-enriched cytoplasmic RNA from carefully dissected rat and mouse hypothalami were prepared. Target cDNA libraries in vector pT7T3D (Pharmacia Biotech, Piscataway, N.J.) and driver libraries in pGEM11Zf (−) (Promega, Madison, Wis.) from analogously prepared cerebellar and hippocampal RNA samples were constructed. The directional tag PCR subtractive hybridization method of Usui and colleagues in Usui et al., supra was applied to produce tagged hypothalamic cDNAs from which cerebellar and hippocampal sequences were depleted in two consecutive steps, removing more than 97% of the input target cDNA. The tag sequences were used as PCR primer-binding sites to amplify the remaining material. An aliquot of the amplified product was cloned into pBCSK$^+$ (Stratagene, La Jolla, Calif.) to generate a subtracted hypothalamus library with 5×10$^5$ members, with inserts ranging from 400 to 1200 (average 700) nucleotide pairs, as judged by agarose gel electrophoresis of the released inserts.

To validate the efficiency of the subtraction, the degree of depletion in the subtracted library of sequences known to be expressed panneurally and the enrichment of sequences known to be expressed specifically in the hypothalamus was determined. Dot blots were prepared with dilutions of cDNA clones of the mRNAs encoding the following proteins: panneural neuron-specific enolase, ubiquitously expressed cyclophilin, hypothalamus-specific vasopressin, hypothalamus-enriched proopiomelanocortin (POMC), thalamus-specific protein kinase C6, and pituitary-specific growth hormone, as well as the target vector itself. The blots were probed with cDNA inserts amplified by PCR from the unsubtracted target library, the subtracted target library or a pool of the driver libraries (FIG. 1). The driver and unsubtracted-library probes gave strong signals for cyclophilin and neuron-specific enolase, and a weaker signal for POMC. Neither hippocampus nor cerebellum is known to express POMC. Although this finding could be explained if one of the drivers had suffered contamination with mRNA from another structure, for example brain stem, the studies below suggest that the signal with the driver libraries was probably due to background hybridization to sequences in the POMC clone. The unsubtracted target additionally gave a weak signal for vasopressin. The subtracted probe gave a very strong signal for vasopressin and POMC and otherwise only faint or undetectable signals. The increase in strength of the vasopressin signal was 20-to-30 fold. Thus, the subtraction protocol removed abundant, panneurally expressed sequences nearly quantitatively while enriching for hypothalamus-specific sequences. There was no apparent contamination with sequences from the anatomically adjacent structures, thalamus or pituitary. The effectiveness of the subtraction was quantitated further by measuring the frequencies of VAT-1 and oxytocin clones in the unsubtracted and subtracted libraries by colony hybridization with a probe corresponding to a mixture of clones of these two species. The frequency of positive clones in the unsubtracted target was 4/2775. After subtraction, the frequency increased to 33/1224. These frequencies indicate an approximately 19-fold increase in the specific activities of these known hypothalamus-enriched species, consistent with the estimates suggested by the data of FIG. 1.

To identify species enriched by the subtraction, 648 clones from the subtracted library were placed into grid arrays and hybridized to three replicate blots of grid images with probes prepared from the unsubtracted or subtracted target library, or a pool of the driver libraries. Approximately 70% of the colonies gave significant signals with the subtracted target probe compared to 50% with the unsubtracted target probe. Only 10% of the colonies gave signals with the mixed-driver probe.

Plasmid DNA was prepared individually from 100 of the colonies that gave strong signals with target-derived probes but no signal with the mixed-driver probe. Partial sequences of the inserts were determined for 94 of these, using a sequencing primer that annealed to the vector region adjacent to the 3' ends of the inserts. The remaining 6 clones were not pursued further because clear sequences were not obtained. More than 90% of the 3' sequences appeared to be derived from bona fide 3' ends of mRNAs as they contained recognizable poly(A)-addition consensus hexads (Birnstiel, M. L., Busslinger, M., & Strub, K. *Cell* 41:349–359, 1985) 12–22 nucleotides upstream from the poly(A) tracts used in their directional cloning. The sequences were searched by BLAST analysis (Altschul, S. F., Gish, W., Miller, W., Myers, E. W., & Lipman, D., *J. Molec. Biol.* 215:403, 1990) against the GenBank database. For those that appeared to be novel, the sequence at the 5' end of the insert was also determined and compared with the database.

A compilation of those data is presented in Table 1 and database accession numbers are given for those prototypes for which a match was found. The 94 clones from the subtracted library for which data were obtained corresponded to 43 distinct mRNA species. Twenty-nine of these were encountered only once in the set of 94 clones, while 14 species were seen between 2 to 13 times. Among the 43 distinct species were 21 that were unambiguously matched to known mRNA species and 22 that were novel species. Amongst the novel species were 6 that appear to correspond (greater than 80% nucleotide sequence identity across an extensive span) to rat homologues of so-called "expressed sequence tags" (ESTs), mRNAs of as yet unknown function compiled in the databases. Two species exhibited similarities in both their partial nucleotide sequences and putative encoded amino acid sequences that suggest them to represent members of protein families: a protein related to the VAT-1 secretory vesicle protein (clone 6), and a new calmodulin-dependent protein kinase (clone 29, SEQ ID NO:5).

The cDNA insert from at least one representative of each of the 43 mRNA species was used as a probe in a Southern blot with lanes corresponding to the hypothalamus, hippocampus and cerebellum target and driver cDNA libraries, each cleaved with the restriction endonuclease HaeIII. Assuming that the cDNA libraries are representative of the mRNAs expressed in their corresponding tissues, this assay serves as a low cost, high throughput surrogate for more expensive and time consuming Northern blot analyses. The hybridization results of the clones in this so-called "cDNA library Southern blot" assay were classified in one of five patterns (Table 1): hybridization to bands detected exclusively in the hypothalamus library (A), to bands highly enriched in hypothalamus but still detectable in hippocampus and cerebellum lanes (B), to bands in hypothalamus and hippocampus but not in cerebellum (C), to bands in all three tissues (D), or too faint to categorize (E). Examples of classes A–D are shown in FIG. 2. Twenty-three of the 43 distinct mRNA species were exclusive to or highly enriched in the hypothalamus library, and an additional 15 species were undetectable in the cerebellum library, indicating the effectiveness of the protocols for identifying species selectively present in the target library. It may be significant that the patterns classified as D corresponded to clones that were isolated only once; similarly, none of the species lacking a poly(A)-addition signal turned up more than once. The existence in the collection of species present in hippocampal, but not cerebellar, libraries presumably is explained by their enrichment during the first subtraction step with cerebellum driver to an extent that did not allow their complete depletion in the second step with hippocampus driver. POMC gave an A pattern in this assay, demonstrating that the driver libraries were not significantly contaminated with POMC-expressing structures. Thus the low POMC signal observed with the driver probes in FIG. 1 is mostly likely accounted for by vector cross-hybridization.

Figure 3A:
Figure 3B:
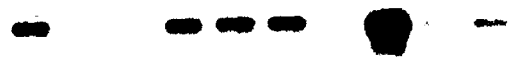
Figure 4A:
FIGS. 4A–4F depict the expression patterns analyzed by in situ hybridization, showing coronal sections of rat brains hybridized with single stranded RNA probes corresponding to the inserts of A, clone 35; B, clone 6; C, clone 10; D, clone 20; E, clone 29 and F, clone 21.
Figure 4B:
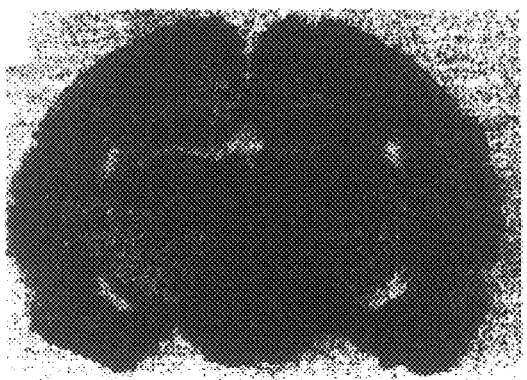
Figure 4C:
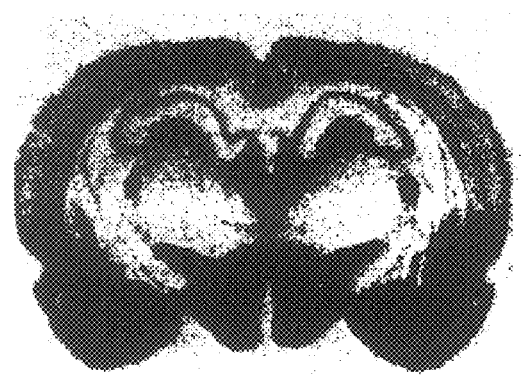
Figure 4D:
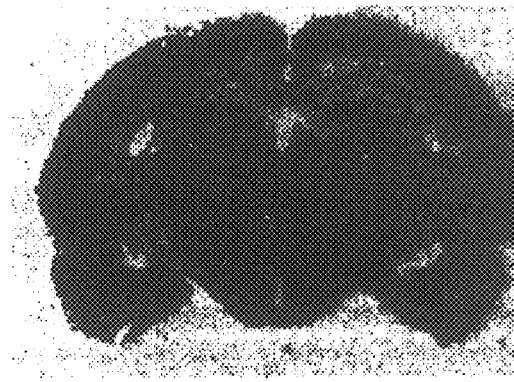
Figure 4E:
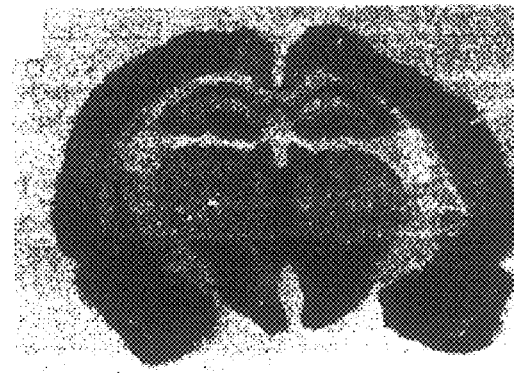
Figure 4F:
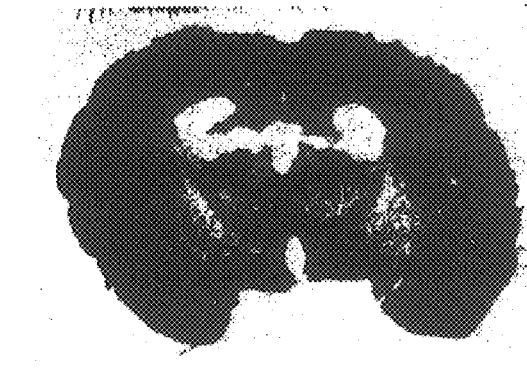

Northern blots were performed for 15 of the species that showed hypothalamus-enriched or -specific distributions (group A or B) in the cDNA Southern blot assay. The blots (FIG. 3) included RNA samples from 6 grossly dissected regions of rat brain in addition to pituitary, liver, kidney and heart. For the clones of species that had been isolated two or more times, the correspondence with the cDNA library Southern blot assay was excellent. Thus, clones 2 (oxytocin) and 35 (novel), which gave A patterns in the cDNA Southern blot study, each detected a band that was strong in the hypothalamus lanes, but only very faint or undetectable in the other lanes. The faint signals were possibly due to low expression in those tissues or to contamination during tissue dissection. Clones 6 (VAT1-like), 10 (novel) and 12 (novel), which had given B patterns, each detected bands that were considerably more intense in the hypothalamus than hippocampus or cerebellum lanes, although each was detected in the pituitary lane (6 strongly) and in the samples from some other structures. Clones 3 (novel), 15 (novel) and 29 (novel calmodulin-dependent protein kinase), although classified originally as B patterns, are more properly considered as C patterns, as their expression profiles in this assay are not enriched in hypothalamus per se, but rather are low in the cerebellum.

The clones encountered only once behaved, as a group, less well. Clones 21 (novel), 37 (novel), 98 (novel) and 99 (kinesin) failed to show substantial enrichment in hypothalamus over hippocampus or cerebellum (although 98 was thalamus enriched). However, clone 33 (novel) detected an RNA species more prevalent in hypothalamus and thalamus than cortex, pons or olfactory bulb and was undetectable in hippocampus, cerebellum or peripheral tissues; thus, technically speaking, clone 33 maintained its A pattern classification. Clone 20 (novel) detected an RNA species with ubiquitous expression but enrichment in hypothalamus and thalamus, thus it is more properly classified as B pattern. Clone 67 (novel) detected a species enriched in hypothalamus and olfactory bulb that was detectable in other brain regions and pituitary but was not detectable in cerebellum.

In situ hybridization on coronal sections of brain from adult male rats was performed using the inserts from clones representing all four classes (A–D): 6, 10, 20, 21, 29 and 35. For all clones, the hybridization pattern was consistent with the Northern blot data. In the A class, the clone 35 mRNA displayed a striking pattern of bilaterally symmetric expression restricted to a few cells in the paraventricular hypothalamic area and ependymal cells surrounding the brain ventricles. No clone 35 signals were detected outside the hypothalamus. The sequence of clone 35 is shown in FIG. 5 and SEQ ID NO. 14.

Clones 6, 10 and 20, belonging to class B, displayed somewhat more complex distributions. Clone 6 gave strong signals in the periventricular hypothalamic nucleus, anterior hypothalamic area, preoptic and arcuate nuclei. Very strong hybridization could also be seen in the centromedial thalamic nucleus and medial habenula. Clone 10 displayed almost the same pattern but additional strong signals could be seen in the laterodorsal thalamic nucleus and dentate gyrus, with weak signals in the hippocampal CA fields and the entire neocortex. Interestingly this mRNA showed a marked enrichment in basal diencephalic structures that included nuclei not only of the hypothalamus but also of the amygdaloid complex. Clone 20 exhibited low levels of expression in several areas of the brain, but displayed especially strong signals in the ventral hypothalamus, most notably in the anterior hypothalamic and periventricular nuclei.

Clone 29 (class C, SEQ ID NO:5), which encodes a novel calmodulin kinase-like protein, was also very strongly expressed in the anterior hypothalamic area and arcuate nucleus, as well as in the pyramidal cell layer of all hippocampal fields and in the medial and central nuclei of the amygdala. The sequence of clone 29 is shown in FIG. 6. Clone 21 represents a class D cDNA, whose distribution includes hypothalamic as well as extrahypothalamic structures. In particular, the clone 21 mRNA was found in cortex, amygdala, hippocampus, caudate, and several thalamic (centrodorsal and reticular nuclei) and hypothalamic nuclei. Within the hypothalamus, clone 21 mRNA was especially abundant in the paraventricular hypothalamic nucleus.

The data compiled in Table 1 suggest that this strategy was effective: 53 of the 94 clones studied were shown to correspond to mRNAs expressed in the hypothalamus at much higher concentrations than in either the hippocampus or cerebellum. An additional 32 of the clones were enriched in both hypothalamus and hippocampus over cerebellum, indicating that the first subtraction was more efficient, probably because the target concentration was higher in the hybridization reaction, thus a greater portion of the common species were driven into hybrids. Cumulatively, 85 of the 94 candidates were found to be enriched in the target hypothalamus compared to the cerebellum, a quite acceptable success rate. It is noteworthy that in 8 cases, the cDNA library Southern blot assay suggested a higher degree of hypothalamus enrichment than was later observed by Northern blotting, presumably due to artifactual enrichment in the target libraries compared to the driver libraries. In a few cases this can be explained by artifactual cloning of an internal or intronic cDNA fragment. Other cases may be explained by difficulties in achieving proportional representation of low prevalence mRNAs in cDNA libraries.

The subtraction steps provided an approximately 30-fold enrichment. In the secondary screen, approximately 60% of the clones were positive with the subtracted probe but not the target probe. Of the 94 clones selected from this screen, 53 were clones of mRNAs selectively expressed in hypothalamus. These 53 clones correspond to approximately 1% of the clones examined in this pilot study, and represented 16 distinct mRNA species, suggesting that a complete characterization of hypothalamus mRNAs might reveal 100–200 species that were specific to or highly enriched in the hypothalamus. Of the 16 mRNA species detected here, 9 corresponded to already known proteins, among them oxytocin, vasopressin and POMC, three neuropeptides known to be highly enriched in the hypothalamus. However, 7 mRNA species were novel. Among mRNA species not detected in the 94-clone sample were those encoding the releasing factors, which are less abundant than most of the species detected here.

Oxytocin and vasopressin mRNAs are predominantly associated with discrete hypothalamic nuclei, as was previously known. The in situ hybridization images indicate that several additional mRNAs, including several novel species, are enriched in the hypothalamus. Among the novel species, only clone 35 meets the hypothesis in its strictest sense: the mRNA appears to be restricted to nuclei in the paraventricular area of the hypothalamus.

Other mRNAs corresponding to novel clones exhibit enrichment in basal diencephalic structures, especially the hypothalamus, but within the hypothalamus none is restricted to a single nucleus. These species presumably encode proteins whose functions are not dedicated to single physiological systems. Nevertheless, their roles seem to have selective utility within the CNS. Previous studies looking at mRNAs enriched in the caudate revealed several involved in signal transduction pathways (Usui, et al., supra). That is not the finding for the hypothalamus-enriched species encountered thus far.

The data suggest that the hypothalamus utilizes at least two different strategies for employing selectively expressed proteins. Some specific mRNAs are discretely correlated to distinct nuclei. Thus far, all of these mRNAs encode secretory signalling proteins. A class of mRNAs have also been recognized that are expressed prominently in hypothalamus and amygdala. These do not appear to be restricted to functionally discrete regions, but their comparable anatomical restrictions suggest that they might participate in a series of biochemical processes that are selectively distributed to these regions, which are developmentally related. Thus these regions may share molecular properties that are not apparent at the anatomical level.

DNA sequence analysis of the complete 569 nucleotide rat clone 35 revealed that the clone mRNA encodes a 130-residue putative secretory protein (called H35) or hypocretin with 4 sites for potential proteolytic maturation (FIG. 5 and see SEQ ID NO. 14). Several proteolytic fragments have been identified, some replacing C-terminal glycines with amide groups. Two of the products of proteolysis have 14 amino acid identities across 20 residues. This region of H35 includes a 7/7 match with a region of the gut hormone secretin, suggesting that the prepropeptide gives rise to two peptide products that are structurally related both to each other and to secretin.

The mouse homolog of clone 35 was also isolated and sequenced (FIG. 5 and see SEQ ID NO. 15). The mouse nucleotide sequence differs in 35 positions relative to the rat sequence and contains 16 additional nucleotides near its 3' end. Of these differences, 19 nucleotides differ within the protein coding region. Only 7 of these affect the encoded protein sequence. One amino acid difference is a neutral substitution in the secretion signal sequence (residue 3). The remaining 6 differences are in the C-terminal region. One of these obliterates a potential proteolytic cleavage site. This observation and the nature of the other differences make it unlikely that 2 of the possible maturation products of the rat preproprotein are functional. However, the 2 peptides that are related both to each other and to secretin are absolutely preserved between species, providing strong support for the notion that these peptides have a function conserved during evolution.

The cells that express this mRNA are distributed in a bilaterally symmetrical pattern in a previously uncharted nucleus of the rat dorsal-lateral hypothalamus and sparse ependymal cells that line the ventricles suggesting that the peptides function as intercellular messengers within the CNS. Colocalization studies suggest a partial overlap with cells positive for galanin, bradykinin and dynorphin. The rat H35 mRNA is restricted to the CNS in the studies performed to date. It is not expressed at high concentrations in immature animals.

These observations, along with the sequence data discussed above, suggest that the H35 peptides are secreted into the CSF and locally within the hypothalamus; that their functions are only manifested in mature animals; and that their expression is coupled to the general homeostatic status of the animal, although not regulated in an all-or-none fashion by homeostasis. In other words, these are new hormones that act within the central nervous system.

The polypeptides may be expressed by transformation of a suitable host cell with a cDNA in a suitable expression vector. The choice of host cell is not critical. The polypeptide may be produced from a procaryotic (e.g. *E. coli*) or eucaryotic (mammalian, e.g. COS-7, CHO, NIH 3T3) host cell, as desired.

The hypocretin polypeptides, and fragments thereof, of this invention are useful in diagnosis and therapy. Recombinant or natural polypeptides may be used in Western blot, ELISA, RIA, and the like, and in receptor binding assays, for direct or competitive binding studies to identify hypocretin specific receptors. The identification of hypocretin analogs and antagonists is also accomplished via use of the polypeptides identified herein. Further details of such uses are described in U.S. Pat. No. 5,242,798, incorporated herein by reference.

In another aspect, the polypeptides of this invention may be used to generate antibodies. Methods of preparing polyclonal antibodies are well known in the art. For example, an immunogenic conjugate comprising the hypocretin protein or a fragment thereof, optionally linked to a carrier protein, is used to immunize a selected mammal (mouse, rabbit, et al.). Serum from the immunized mammal is collected and treated to separate the immunoglobulin fraction. Monoclonal antibodies are prepared by standard hybridoma cell technology (Koller and Milstein, *Nature* 256:495–497 (1975)). Briefly, spleen cells are obtained from a host animal immunized with an hypocretin protein or fragment. Hybrid cells are formed by fusing these spleen cells with an appropriate myeloma cell line and cultured. The antibodies produced are screened for their ability to bind H35 by, for example, ELISA. The cells producing the hypocretin antibody are selected.

Antibodies directed to a conserved epitope common to the hypocretin polypeptides of several species will detect hypocretin polypeptides of mammalian species in general. For example, antibodies directed against such a conserved sequence as GNHAAGILT (SEQ ID NO: 13; FIG. 5B) can be used to detect human hypocretin polypeptides.

The polynucleotides and polypeptides of this invention may also be formulated into diagnostic and therapeutic compositions. Representative methods of formulation may be found in *Remington: The Science and Practice of Pharmacy*, 19th ed., Mack Publishing Co., Easton, Pa. (1995). The selection of the precise concentration, composition, and delivery regimen is influenced by, inter alia, the specific pharmacological properties of the selected compound, the intended use, the nature and severity of the condition being treated or diagnosed, and the physical condition and mental acuity of the intended recipient. Such considerations are within the purview of the skilled artisan.

Representative delivery regimens include oral, parenteral (subcutaneous, intramuscular, and intravenous), rectal, buccal, pulmonary, transdermal, and intranasal, preferably intravenous. The composition may be in solid, liquid, gel, or aerosol form. Generally, the compound will be present in an amount from about 1 $\mu$g to about 100 $\mu$g, in a sterile aqueous solution, optionally including stabilizers and the like.

The present invention also describes a diagnostic system, preferably in kit form, for assaying for the presence of a hypocretin of this invention in a body sample, such brain tissue, cell suspensions or tissue sections, or body fluid samples such as CSF, blood, plasma or serum, where it is desirable to detect the presence, and preferably the amount, of a hypocretin protein in the sample according to the diagnostic methods described herein.

In a related embodiment, a nucleic acid molecule can be used as a probe (an oligonucleotide) to detect the presence of a gene or mRNA in a cell that is diagnostic for the presence or expression of a hypocretin in the cell. The nucleic acid molecule probes were described in detail earlier.

The diagnostic system includes, in an amount sufficient to perform at least one assay, a subject hypocretin polypeptide, a subject antibody or monoclonal antibody, and a subject nucleic acid molecule probe of the present invention, as a separately packaged reagent.

Another embodiment is a diagnostic system, preferably in kit form, for assaying for the presence of a hypocretin polypeptide or anti-hypocretin antibody in a body fluid sample such as for monitoring the fate of therapeutically administered hypocretin polypeptide or anti-hypocretin antibody. The system includes, in an amount sufficient for at least one assay, a subject hypocretin polypeptide and a subject antibody as a separately packaged immunochemical reagent.

Instructions for use of the packaged reagent(s) are also typically included.

As used herein, the term "package" refers to a solid matrix or material such as glass, plastic (e.g., polyethylene, polypropylene or polycarbonate), paper, foil and the like capable of holding within fixed limits a polypeptide, polyclonal antibody or monoclonal antibody of the present invention. Thus, for example, a package can be a glass vial used to contain milligram quantities of a hypocretin polypeptide or antibody or it can be a microliter plate well to which microgram quantities of a contemplated polypeptide or antibody have been operatively affixed, i.e., linked so as to be capable of being immunologically bound by an antibody or antigen, respectively.

"Instructions for use" typically include a tangible expression describing the reagent concentration or at least one assay method parameter such as the relative amounts of reagent and sample to be admixed, maintenance time periods for reagent or sample admixtures, temperature, buffer conditions and the like.

A diagnostic system of the present invention preferably also includes a label or indicating means capable of signaling the formation of an immunocomplex containing a polypeptide or antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-diethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in *Antibody As a Tool*, Marchalonis, et al., eds., John Wiley & Sons, Ltd., pp. 189–231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-amino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such as $^{111}In$ or $^{3}H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas, et al., *Scand. J. Immunol.*, Vol. 8 Suppl. 7:7–23 (1978), Rodwell et al., *Biotech.*, 3:889–894 (1984), and U.S. Pat. No. 4,493,795.

The diagnostic systems can also include, preferably as a separate package, a specific binding agent. A "specific binding agent" is a molecular entity capable of selectively binding a reagent species of the present invention or a complex containing such a species, but is not itself a polypeptide or antibody molecule composition of the present invention. Exemplary specific binding agents are second antibody molecules, complement proteins or fragments thereof, *S. aureus* protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent species-containing complex.

The diagnostic kits of the present invention can be used in an "ELISA" format to detect the quantity of hypocretin in a sample. "ELISA" refers to an enzyme-linked immunosorbent assay that employs an antibody or antigen bound to a solid phase and an enzyme-antigen or enzyme-antibody conjugate to detect and quantify the amount of an antigen present in a sample. A description of the ELISA technique is found in Chapter 22 of the 4th Edition of *Basic and Clinical Immunology* by D. P. Sites et al., published by Lange Medical Publications of Los Altos, Calif. in 1982 and in U.S. Pat. No. 3,654,090; U.S. Pat. No. 3,850,752; and U.S. Pat. No. 4,016,043, which are all incorporated herein by reference.

In some embodiments, a hypocretin polypeptide, an antibody or a monoclonal antibody of the present invention can be affixed to a solid matrix to form a solid support that comprises a package in the subject diagnostic systems.

A reagent is typically affixed to a solid matrix by adsorption from an aqueous medium although other modes of affixation applicable to proteins and polypeptides can be used that are well known to those skilled in the art. Exemplary adsorption methods are described herein.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron ($\mu$) to about 5 millimeters (mm) in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microliter plate such as those made from polystyrene or polyvinylchloride.

The reagent species, labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microliter plate and one or more buffers can also be included as separately packaged elements in this diagnostic assay system.

The packaging materials discussed herein in relation to diagnostic systems are those customarily utilized in diagnostic systems.

G. Cell Lines Expressing Hypocretin

The invention also includes a host cell transformed with a recombinant DNA (recombinant DNA) molecule of the present invention. The host cell can be either procaryotic or eucaryotic, although eucaryotic cells are preferred, particularly mammalian cells. Preferred cells are isolated, that is, substantially homogeneous and therefore free from other cell types or other cells having a hypocretin protein expressed therein.

A cell expressing a hypocretin of this invention has a variety of uses according to this invention. Particularly preferred are uses for bulk production of hypocretin, for the purpose of providing immunogen for production of antibody, for supply of therapeutic protein, for direct binding or for screening pharmaceutical compound banks for the presence of hypocretin receptor-specific ligands, i.e., in drug screening assays as described herein. Thus, particularly preferred are cells containing a recombinant DNA molecule that expresses a hypocretin protein of this invention.

In one embodiment, a cell is produced for transplantation into a body tissue, thereby expressing hypocretin and providing replacement therapy. The cell can be syngeneic, and typically will be a brain tissue-derived cell, such as a hippocampal cell, neonatal brain tissue cell, glioma and the like neuronal tissue cell. Transplantation is accomplished using surgical procedures available to a neurosurgeon where the transplantation is to be made into the brain, brain stem or other neurological tissues. In preferred embodiments, the cell contains a vector for expressing the hypocretin in which the expression means is under the control of a regulatable promoter, as is well known, such that expression of the hypocretin protein can be regulated.

Eucaryotic cells useful for expression of a hypocretin protein are not limited, so long as the cell or cell line is compatible with cell culture methods and compatible with the propagation of the expression vector and expression of the hypocretin protein gene product. Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61, NIH Swiss mouse embryo cells NIH/3T3 (ATCC CRL 1658), HELA cells (ATCC CCL 2), baby hamster kidney cells (BHK), COS-7, COS-1, HEK293 (ATCC CRL 1573), Ltk-1, AV-12 (ATCC CRL 9595), and the like eucaryotic tissue culture cell lines.

Transformation of appropriate cell hosts with a recombinant DNA molecule of the present invention is accomplished by well known methods that typically depend on the type of vector used. With regard to transformation of procaryotic host cells, see, for example, Cohen et al., *Proc. Natl. Acad. Sci. USA*, 69:2110 (1972); and Maniatis et al., *Molecular Cloning, A Laboratory Mammal*, Cold Spring Harbor Laboratory, Cold Spring Harbor, N.Y. (1982).

With regard to transformation of vertebrate cells with vectors containing recombinant DNAs, see, for example, Graham et al., *Virol.*, 52:456 (1973); Wigler et al., *Proc. Natl. Acad. Sci. USA*, 76:1373–76 (1979), and the teachings herein.

Successfully transformed cells, i.e., cells that contain a recombinant DNA molecule of the present invention, can be identified by well known techniques. For example, cells resulting from the introduction of an recombinant DNA of the present invention can be cloned to clonally homogeneous cell populations that contain the recombinant DNA. Cells from those colonies can be harvested, lysed and their DNA content examined for the presence of the recombinant DNA using a method such as that described by Southern, *J. Mol. Biol.*, 98:503 (1975) or Berent et al., *Biotech.*, 3:208 (1985).

In addition to directly assaying for the presence of recombinant DNA, successful transformation can be confirmed by well known immunological methods when the recombinant DNA is capable of directing the expression of hypocretin or by the detection of hypocretin binding activity.

For example, cells successfully transformed with an expression vector produce proteins displaying hypocretin antigenicity or biological activity. Samples of cells suspected of being transformed are harvested and assayed for either hypocretin biological activity or antigenicity.

In addition to the transformed host cells themselves, the present invention also includes a culture of those cells, preferably a monoclonal (clonally homogeneous) culture, or a culture derived from a monoclonal culture, in a nutrient medium. Preferably, the culture also contains a protein displaying hypocretin antigenicity or biological activity.

Nutrient media useful for culturing transformed host cells are well known in the art and can be obtained from several commercial sources. In embodiments wherein the host cell is mammalian, a "serum-free" medium can be used.

H. Screening Methods to Identify Agonists and Antagonists of Hypocretin

The ability to selectively bind/modulate function of a hypocretin receptor by a hypocretin ligand is at the heart of useful hypocretin pharmacology, and depends on identifying pharmacological molecules which can act a selective ligands, agonists or antagonists for a hypocretin receptor. To that end, the elucidation of new hypocretin proteins, such as those described herein, provides valuable tools for the search for selective reagents, tools that are useful in binding assays, and in screening assays which indicate selective drug response to the hypocretin receptor.

The invention includes methods for determining whether a molecule binds to, and preferably whether the molecule activates, a preselected hypocretin receptor.

The method comprises conducting a binding assay to identify molecules which bind the hypocretin receptor, as described in any of the assays herein. Thus, the method comprises (1) contacting a candidate molecule with a cell having a hypocretin receptor under conditions permitting binding of hypocretin to the receptor, and (2) detecting the presence of the candidate molecule bound to the hypocretin receptor, thereby determining whether the candidate binds to the receptor. The receptor is typically a cell surface protein when expressed by the cells.

Alternatively, one can use a competition format to identify analogs of hypocretin by using a labeled hypocretin, and measuring the amount of bound label in the presence of a candidate ligand, indicating whether the candidate competes with labeled hypocretin for binding to the receptor. An exemplary competition assay is described herein.

It is also possible to use the above method to determine whether the molecule which binds to the hypocretin receptor also activates or motivates the receptor's function, i.e., acts as an agonist, or determine whether the molecule inhibits the receptor's function, i.e., acts as an antagonist, or acts as and inverse agonist. Thus, by evaluating in the detecting step whether the hypocretin receptor is activated, one determines whether the candidate molecule is bioactive.

Methods for detecting bioactivity of the candidate molecule can vary, but typically involve measuring changes in intracellular levels of a secondary messenger effected as a result of binding, detecting changes in electrical potential, observing physiological or behavioral effects related to hypocretin function, and the like methods. Exemplary assays for binding or for hypocretin-specific bioactivity are described in the Examples and include measurement of electrical changes of hypothalamic neurons, measurement of food intake or body temperature, or direct binding to a cell having a hypocretin receptor.

It is noted that the hypocretin receptor has not been characterized in extensive detail. Thus, any receptor that binds hypocretin can be referred to as a hypocretin receptor for the purposes of a screening assay, although receptors with the highest affinity and specificity for hypocretin are preferred. In practicing the present screening methods, one can use any of a variety of cells lines or tissues that possess a hypocretin receptor, including the exemplary cell lines and tissues described herein. The invention should not be construed as limiting so long as the binding or bioactivity assay involves the use of a hypocretin receptor. In preferred embodiments, a receptor that is specific for hypocretin should be used. Specificity can be demonstrated by well known methods of ligand binding and ligand-mediated activation.

A related embodiment includes a method for screening to identify a candidate molecule that can bind, inhibit or activate a preselected hypocretin receptor by functioning as a hypocretin agonist or antagonist. The method comprises:

(a) contacting a mammalian cell with said candidate drug under conditions permitting activation of said hypocretin receptor by hypocretin; and (b) detecting the activation status of said hypocretin receptor, and thereby determining whether the drug activates or inhibits said receptor.

I. Methods for Altering Hypocretin Receptor Function a. Therapeutic Methods

The certain reagents described in the present invention have the capacity to modulate hypocretin receptor function, such as agonists or antagonists, and therefore are useful in therapeutic methods for conditions mediated by the hypocretin receptor.

Hypocretin polypeptides that mimic exposed regions of hypocretin have the ability to function as analogs and compete for binding to the hypocretin receptor, or for other agents that would normally interact with the receptor, thereby inhibiting binding of hypocretin to the receptor.

Furthermore, antibodies and monoclonal antibodies of the present invention that bind to exposed regions of hypocretin have the capacity to alter hypocretin receptor function by blocking natural interactions with hypocretin that normally interact at the site. Exemplary antibodies are the anti-hypocretin antibodies described earlier.

Finally, oligonucleotides are described herein which are complementary to mRNA that encodes a hypocretin protein of this invention and that are useful for reducing gene expression and translation of the hypocretin mRNA, thereby altering hypocretin levels in a tissue.

In one embodiment, the present invention provides a method for modulating hypocretin function in an animal or human patient comprising administering to the patient a therapeutically effective amount of a physiologically tolerable composition containing a hypocretin polypeptide, analog or peptidomimetic, anti-hypocretin antibody or monoclonal antibody, hypocretin agonist or antagonist, or an oligonucleotide of the present invention.

A therapeutically effective amount of a hypocretin polypeptide, as an example for practicing the invention, is a predetermined amount calculated to achieve the desired effect, i.e., to modulate receptor interaction with its normal target, and thereby interfere with normal receptor function. Depending on the structure of the particular peptide the binding of some peptides will activate the receptor, while binding of other peptides will not activate the receptor.

Similarly, a therapeutically effective amount of an anti-hypocretin antibody is a predetermined amount calculated to achieve the desired effect, i.e., to immunoreact with the hypocretin, and thereby inhibit the hypocretin receptor's ability to interact with its normal target, hypocretin, and thereby interfere with normal receptor function.

The in vivo inhibition of hypocretin receptor function using a hypocretin polypeptide, an anti-hypocretin antibody, or hypocretin agonist or antagonist of this invention is a particularly preferred embodiment and is desirable in a variety of clinical settings, such as where the patient is exhibiting symptoms of an over or under activated hypocretin receptor.

A therapeutically effective amount of a hypocretin polypeptide, agonist or antagonist of this invention is typically an amount such that when administered in a physiologically tolerable composition is sufficient to achieve a plasma concentration of from about 0.1 nanomolar (nM) to about 100 nM, and preferably from about 0.5 nM to about 10 nM.

A therapeutically effective amount of an antibody of this invention is typically an amount of antibody such that when administered in a physiologically tolerable composition is sufficient to achieve a plasma concentration of from about 0.1 microgram ($\mu$g) per milliliter (ml) to about 100 $\mu$/g/ml, preferably from about 1 $\mu$g/ml to about 5 $\mu$g/ml, and usually about 5 $\mu$g/ml.

The effectiveness of the therapy can be determined by observing ablation of the symptoms associated with the function of the hypocretin receptor being inhibited.

The therapeutic compositions containing a hypocretin polypeptide, agonist, antagonist or anti-hypocretin antibody of this invention are conventionally administered intravenously or by a method for delivery to a brain tissue, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

Delivery to a brain tissue or CSF can be accomplished by a variety of means, including by direct injection, by use of a cannula into the target tissue, by direct application in a surgical procedure, by adsorption across the blood-brain barrier following intravenous administration, by viral vectors, and the like means.

The therapeutic compounds and compositions are generally administered so as to contact the cells or the tissue containing cells which contain the target hypocretin receptor. This administration can be accomplished by introduction of the composition internally such as orally, intravenously, intramuscularly, intranasally or via inhalation of aerosols containing the composition, and the like, by cannula into a brain tissue, or by introduction into or onto a tissue system as by introduction transdermally, topically or intralesionally, in suppositories, or by intra-orbital injection, and the like.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are particular to each individual. However, suitable dosage ranges for systemic application are disclosed herein and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations in the CSF or blood in the ranges specified for in vivo therapies are included.

As an aid to the administration of effective therapeutic amounts of a hypocretin polypeptide, agonist, antagonist, antibody, or monoclonal antibody, (hereinafter a "therapeutic agent") a diagnostic method of this invention for detecting a therapeutic agent in the subject's CSF or blood is useful to characterize the fate of the administered therapeutic agent. Suitable diagnostic (monitoring) assays are described herein.

b. Methods for Inhibiting Gene Expression

In another embodiment, the invention includes the use of nucleic acids encoding portions of a hypocretin gene for inhibiting gene expression and function.

The present invention provides for a method for inhibiting expression of hypocretin gene products and thereby inhibiting the function of the target hypocretin protein. The DNA segments and their compositions have a number of uses, and may be used in vitro or in vivo. In vitro, the compositions may be used to block function and expression of hypocretin in cell cultures, tissues, organs and the like materials that can express hypocretin. In vivo, the compositions may be used prophylactically or therapeutically for inhibiting expression of a hypocretin gene, and by inhibiting diseases or medical conditions associated with the expression or function of the hypocretin gene or the activity state of its receptor.

The method comprises, in one embodiment, contacting cells or tissues with a therapeutically effective amount of a pharmaceutically acceptable composition comprising a DNA segment of this invention. In a related embodiment, the contacting involves introducing the DNA segment composition into cells expressing a hypocretin protein.

The DNA segment can be in a variety of forms, but is preferably in a single-stranded form to facilitate complementary hybridization to the target mRNA in the cell in which the hypocretin gene expression is to be altered.

The term "cells" is intended to include a plurality of cells as well as single cells. The cells can be isolated, or can be cells that form a larger organization of cells to form a tissue or organ.

Another embodiment is a method of inhibiting the expression of hypocretin genes in a patient comprising administration to the patient of a therapeutically effective amount of a DNA segment composition of this invention in a pharmaceutically acceptable excipients. In cases where the distribution of the hypocretin is believed to be disseminated in the body, the administration of therapeutic oligonucleotide can be systemic. Alternatively, the target hypocretin can be localized to a tissue, and the therapeutic method can likewise be directed at delivering the therapeutic DNA segment to the tissue to be treated.

The concentration of the active DNA segment ingredient in a therapeutic composition will vary, depending upon the desired dosage, use, frequency of administration, and the like. The amount used will be a therapeutically effective amount and will depend upon a number of factors, including the route of administration, the formulation of the composition, the number and frequency of treatments and the activity of the formulation employed.

The use of therapeutic DNA segments, and therefore the delivery of those DNA segments into cells where they are effective, has been described in a variety of settings. It is generally known that therapeutically effective intracellular levels of nucleic acids, and particularly smaller nucleic acids such as DNA segments and oligonucleotides, can be achieved by either exposing cells to solutions containing nucleic acids or by introduction of the nucleic acids into the inside of the cell. Upon exposure, nucleic acids are taken up by the cell where they exert their effectiveness. In addition, direct introduction into the cell can be provided by a variety of means, including microinjection, delivery by the use of specific uptake vehicles, and the like.

The pharmaceutical composition containing the therapeutic oligonucleotide preferably also contains physiologically acceptable carriers, in particular hydrophobic carriers which facilitate carrying the oligonucleotide through the cell membrane or blood brain barrier.

Exemplary descriptions of the delivery of therapeutic DNA segments and oligonucleotides into cells can be found in the teachings of U.S. Pat. Nos. 5,04,820, 4,806,463, 4,757,055, and 4,689,320, which teachings are hereby incorporated by reference.

A therapeutically effective amount is a predetermined amount calculated to achieve the desired effect, i.e., to bind to a hypocretin gene present and thereby inhibit function of the gene.

As is apparent to one skilled in the art, the copy number of a hypocretin gene may vary, thereby presenting a variable amount of target with which to hybridize. Thus it is preferred that the therapeutic method achieve an intracellular concentration of a therapeutic DNA segment of this invention in molar excess to the copy number of the gene in the cell, and preferably at least a ten-fold, more preferably at least a one-hundred fold, and still more preferably at least a one thousand-fold excess of therapeutic DNA segments relative to the gene copy number per cell. A preferred effective amount is an intracellular concentration of from about 1 nanomolar (nM) to about 100 micromolar ($\mu$M), particularly about 50 nM to about 1 $\mu$M.

Alternatively, a therapeutically effective amount can be expressed as an extracellular concentration. Thus it is preferred to expose a cell containing a hypocretin gene to a concentration of from about 100 nM to about 10 millimolar (mM), and preferably about 10 $\mu$M to 1 mM. Thus, in embodiments where delivery of a therapeutic DNA segment composition is designed to expose cells to the nucleic acid for cellular uptake, it is preferred that the local concentration of the DNA segment in the area of the tissue to be treated reach the extracellular concentrations recited above.

For patient dosages, using a 20 nucleotide base double-stranded DNA segment as the standard, a typical dosage of therapeutic composition for a 70 kilogram (kg) human contains in the range of about 0.1 milligram (mg) to about 1 gram of 20-mer DNA segment per day, and more usually in the range of about 1 mg to 100 mg per day. Stated differently, the dosage is about 1 $\mu$g/kg/g day to about 15 mg/kg/day, and preferably about 15 to 1500 $\mu$g/kg/day.

The in vivo inhibition of hypocretin gene expression and function by a therapeutic composition of this invention is desirable in a variety of clinical settings, such as where the patient is at risk for disease based on expression of the hypocretin gene.

c. Therapeutic Compositions

The present invention includes therapeutic compositions useful for practicing the therapeutic methods described herein. Therapeutic compositions of the present invention contain a physiologically tolerable carrier together with a therapeutic reagent of this invention, namely a hypocretin polypeptide, an anti-hypocretin antibody or monoclonal antibody, or oligonucleotide as described herein, dissolved or dispersed therein as an active ingredient. In a preferred embodiment, the therapeutic composition is not immunogenic when administered to a mammal or human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like.

The preparation of a pharmacological composition that contains active ingredients dissolved or dispersed therein is well understood in the art. Typically such compositions are prepared as injectables either as liquid solutions or suspensions, however, solid forms suitable for solution, or suspensions, in liquid prior to use can also be prepared. The preparation can also be emulsified.

The active ingredient can be mixed with excipient which are pharmaceutically acceptable and compatible with the active ingredient and in amounts suitable for use in the therapeutic methods described herein. Suitable excipient are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes.

As described herein, for intracellular delivery of oligonucleotides, specialized carriers may be used which facilitate transport of the oligonucleotide across the cell membrane. These typically are hydrophobic compositions, or include additional reagents which target delivery to and into cells.

Liquid compositions can also contain liquid phases in addition to and to the exclusion of water. Exemplary of such additional liquid phases are glycerin, vegetable oils such as cottonseed oil, and water-oil emulsions.

A therapeutic composition contains an amount of a hypocretin polypeptide or anti-hypocretin antibody molecule of the present invention sufficient to inhibit hypocretin function. Typically this is an amount of at least 0.1 weight percent, and more preferably is at least 1 weight percent, of peptide or antibody per weight of total therapeutic composition. A weight percent is a ratio by weight of peptide or antibody to total composition. Thus, for example, 0.1 weight percent is 0.1 grams of polypeptide per 100 grams of total composition.

The following Examples are illustrative of one means of practicing certain aspects of the invention disclosed herein and should not be construed so as impart any undue limitations upon the invention as claimed below.

EXAMPLE 1

Young adult Sprague-Dawley rats of both genders were sacrificed under anesthesia by decapitation and their brains quickly removed. The hypothalamus, hippocampus, and cerebellum were immediately dissected on an ice-cold plate following the boundaries described by Glowinski and Iversen (Glowinski, J., & Iversen, L. L., *J. Neurochem.* 13:655–669, 1966). The block of hypothalamic tissue was 2 mm deep and was taken using the optic chiasm as the rostral limit and the mammillary bodies as caudal reference. Cytoplasmic RNA was isolated rapidly from the dissected tissues (Schibler, K., Tosi, M., Pittet, A. C., Fabiani, L., & Wellauer, P. K., *J. Mol. Biol.* 142:93–116, 1980) and enriched for poly(A)-containing species by oligo(dT)-cellulose chromatography (Aviv, H., & Leder, P., *Proc. Natl. Acad. Sci. USA* 69:1408–1412, 1972). For the Northern blots, RNA was isolated (Chirgwin, J. M., Przybyla, A. E., MacDonald, R. J., & Rutter, W. J., *Biochemistry* 18:5294, 1979) from frozen tissue purchased from Zivic-Miller (Zelienople, Pa.). cDNA libraries were prepared as described previously Usui et al, supra, except that pBCSK$^+$ was used for the subtracted library rather than pT7T3D because lower backgrounds have been found in the subsequent steps using the former vector (H. Usui, personal communication). The number of recombinants in the libraries were: pT7T3D hypothalamus $8 \times 10^6$; cerebellum pGEM11Zf (−) $5 \times 10^5$; hippocampus pGEM11Zf (−) $1 \times 10^6$.

Subtractive hybridization was performed in two cycles using the previously described procedure (Usui et al., supra). Briefly, 1 µg of trace-labeled, tagged hypothalamus target cDNA prepared as described from the pT7T3D target library was annealed for 24 hrs at 68 degree Celsius in 10 µl of hybridization buffer (Usui et al, supra) with 20 µg cerebellum cRNA (ratio 1:20). After hydroxyapatite chromatography, the single-stranded fraction corresponded to 10% of the input material, as judged by tracer quantitation. This was mixed with 20 µg of hippocampus cRNA (estimated ratio 1:200) for a second 24 hr hybridization, after which 30% of the input chromatographed at the single-strand position. Cumulatively, these steps removed more than 97% of the input tracer. An aliquot of the single-stranded material was used as template in a 30-cycle PCR (program: 94 degree Celsius for 15 sec, 60 degree Celsius for 15 sec, 72 degree Celsius for 1 min) using primers corresponding to the tag sequences (Usui et al., supra): 5'-AACTGGAAGAATTCGCGG-3' (SEQ ID NO: 19) and 5'-AGGCCAAGAATTCGGCACGA-3' (SEQ ID NO: 16). The amplification product was cleaved with NotI, then EcoRI, and inserted into pBCSK$^+$. A dot blot was prepared and screened with probes prepared from the target, subtracted target and driver libraries as previously described by Usui et al, supra, using serial dilutions of plasmid cDNA clones isolated previously in this laboratory. The target and subtracted target cDNA libraries were screened to determine the frequency of oxytocin and VAT-1 cDNA clones using as probes clones isolated in the present study.

Clone 35 cDNA from the subtracted rat hypothalamus library was used as a probe to screen a rat brain cDNA library in the plasmid pHG327 as described by Forss-Petter et al., *J. Mol. Neurosci.* 1:63–75 (1989). The cDNA library was constructed as described by Staeheli et al., *Cell* 44:147–158 (1986).

EXAMPLE 2

Similarly, following the procedures of Example 1, a mouse (C57/B16) hypothalamus cDNA library, constructed in the pT7T3D vector, was used as a template for PCR amplification (primers 5' TAAGACGACGGCCTCAG 3', SEQ ID NO: 17, and 5' CACACCAACAGAGAAACG 3', SEQ ID NO: 18) to obtain the mouse homolog of the rat H35 cDNA obtained above. The mouse and rat cDNA (SEQ ID NO: 15 and SEQ ID NO: 14, respectively) and protein sequences (mouse SEQ ID NO:2; rat SEQ ID NO: 1) are compared in FIG. 5. The 569 nucleotide rat sequence has the potential to encode a 130-residue putative secretory protein (preprohypocretin) with an apparent signal sequence and 3 additional sites for potential proteolytic maturation (FIG. 5A). Two of the putative products of proteolysis (hcrt1, SEQ ID NO: 7 and hcrt2, SEQ ID NO: 9) have 14 amino acid identities across 20 residues (FIG. 5B). This region of one of the peptides contains a 7/7 match with secretin (FIG. 5B, SEQ ID NO: 21), suggesting that the prepropeptide gives rise to two peptide products that are structurally related both to each other and to secretin.

The mouse hypocretin nucleotide sequence (SEQ ID NO: 15) differs in 35 positions relative to the rat (SEQ ID NO: 14), and contains 16 additional nucleotides near its 3' end. Of these differences, 19 are within the putative protein-coding region (FIG. 5A), only 7 of which affect the encoded protein sequence: one amino acid difference at residue 3 is a neutral substitution in the apparent secretion signal sequence; the remaining 6 differences are near the C-terminus, one of which obliterates a potential proteolytic cleavage site. The absence of this site and the nature of the other differences make it unlikely that two of the four possible rat maturation products are generated and functional in mice. However, the two putative hcrt peptides that are related both to each other and to the secretin family are absolutely preserved between the two species, providing strong support for the notion that these peptides have a function conserved during evolution. Both hcrt1 and hcrt2 terminate with glycine residues, leaving the nitrogen of the terminal glycine as a C-terminal amide in the mature peptide.

Several hypocretin peptides are distinguished within the sequence of hypocretin (FIG. 5). The peptide from about amino acid residue 28 to about amino acid residue 130 (SEQ ID NO:6) represents the peptide produced by cleavage of the signal peptide. The peptide from about amino acid residue 28 to about amino acid residue 66 (SEQ ID NO:7) corresponds to hcrt1. The peptide from about amino acid residue 28 to about amino acid residue 65 (SEQ ID NO:8) corresponds to hcrt1 matured by peptidylglycine alpha-amidating monooxygenase, leaving the nitrogen of the terminal glycine as a C-terminal amide in the mature peptide. The peptide from about amino acid residue 70 to about amino acid residue 97 (SEQ ID NO:9) corresponds to hcrt2. The peptide from about amino acid residue 70 to about amino acid residue 96 (SEQ ID NO:10) corresponds to hcrt2 matured by peptidylglycine alpha-amidating monooxygenase, leaving the nitrogen of the terminal glycine as a C-terminal amide in the mature peptide. The peptide from about amino acid residue 47 to about amino acid residue 66 (SEQ ID NO:11) corresponds to the consensus sequence region of hcrt1 (FIG. 5B). The peptide from about amino acid residue 78 to about amino acid residue 97 (SEQ ID NO:12) corresponds to the consensus region of Hrct2. The peptide GNHAAGILT (SEQ ID NO:13) is common to both hcrt1 and hcrt2.

EXAMPLE 3

Rat H35 (SEQ ID NO:3) is inserted into the BamH1 sites of a pHG237 vector. Upon digestion with BamH1 restriction enzyme, the resultant 569 bp fragment is then inserted directly into the BglII site of the polylinker region of the pCM 4 vector (D. Russell, U. Texas Southwestern Medical Center, Dallas, Tex.), which uses the cytomegalovirus (CMV) promoter. Several eight to ten amino acid epitope tags are added by PCR to the C-terminus of H35 to allow visualization of the expressed product.

The respective 5' and 3' primers, 5' ATCGAGATCTAGA-CACCATG AACCTTCCTTCTACAAAGGTT 3' (SEQ ID NO: 22) and 5' ACTGTCTA GATCATAGATCTTCTTCA-G A A A T A A G T T T T T G T T C G A C T C T G G A T C-CGCCCCGGG GCGCT 3' (SEQ ID NO: 23), are used as primers to amplify H35 beginning at position 85 in SEQ ID NO:3 with an inserted BglII site added at its 5' end to the 3' end having an inserted c-myc epitope tag. The PCR products are subcloned into pCMV and transfected into a mammalian host cell to produce an H35-myc tagged protein product.

H35 proteins are also produced in bacteria by subcloning the H35 coding sequence into pRSET B (Invitrogen, San Diego, Calif.), which encodes six histidines prior to the H35 sequence. The vector contains a T7 promoter which drives expression of 6×His-tagged proteins in $E.$ $coli$. The respective 5' and 3' oligonucleotides 5' ATCGAGATCTCT-TGGGGTGGACGCGCAGCCT 3' (SEQ ID NO: 24) and 5' ACTGAATTCTCAGACTCTGGATCCGCCCCG 3' (SEQ ID NO: 25) are used as PCR primers to amplify the rat H35 sequence into the BglII and EcoRI sites of the pRSET B vector. The resulting hypocretin-poly-(His) fusion protein may be purified by affinity chromatography on a metal affinity resin.

An H35-glutathione-S-transferase fusion protein is produced in $E.$ $coli$ by subcloning the H35 sequence into a pGEX2 vector (Pharmacia).

EXAMPLE 4

The mouse Hcrt gene was mapped to Chromosome 11 using an interspecific backcross. A single-strand sequence polymorphism between C57BL/6J and SPRET/Ei was detected as previously described and mapped on The Jackson Laboratory BSS panel. An Hcrt-specific product of approximately 600 base pairs was amplified from mouse C57BL/6J genomic DNA using synthetic oligonucleotides 5'-GACGGCCTCAGACTTCTTGG-3' (SEQ ID NO: 26) and 5'-GCAACAGTTCGTAGAGACGG-3' (SEQ ID NO: 27). This product contained a putative intron, and its identity as hcrt was confirmed by sequencing (data not shown). Genotype data and references for these and other linked markers can be accessed via the Mouse Genome Database (http://www.informatics.jax.org).

No recombinants in 94 BSS mice were found between hcrt and the previously mapped loci Brca1, Tubg and Mpmv8, placing Hcrt maximally within 3.8 cM (95% confidence limit) of these genes. The Hoxb cluster is approximately 1 cM centromeric to Hcrt, and the Kcnj2 gene is located approximately 4 cM telomeric. Hcrt is located in the portion of mouse Chromosome 11 that shows conserved synteny with human Chromosome 17q21-q24.

In Northern blot studies using poly(A)$^+$ RNA prepared from brain and different peripheral tissues, the 700-nucleotide hypocretin mRNA was detected only in brain samples. Previous studies with RNA from different regions of the brain had detected the hypocretin mRNA predominantly in hypothalamus samples. In samples of RNA from whole brains of developing rats, hypocretin mRNA was detected at low concentrations as early as embryonic day 18, but increased in concentration dramatically after the third postnatal week. There was no detectable difference between brain samples from adult males and females, suggesting that the late onset was not related to sexually dimorphic processes. In situ hybridization studies detected cell bodies in the dorsal-lateral hypothalamus and in cells that line the ventricles.

EXAMPLE 5

A polyclonal antiserum (serum 2050) was raised to a chemically synthesized peptide corresponding to the C-terminal 17 amino acid residues (CPTATATACAPRGGSRV, SEQ ID NO: 28) of the rat preprohypocretin sequence. In Western transfer blots using as target electrophoretically separated proteins from bacteria transformed with the plasmid pRSET B engineered to express preprohypocretin, a single prominent immunoreactive band was observed with a migration of approximately 19 kDa with the hyperimmune serum, but not with the preimmune serum. No immunoreaction was detected with an extract from bacteria transformed with a preprohypocretin/pRSET B expression plasmid, indicating that detection of the 19 kDa target requires hypocretin expression. Analogous results were obtained with an additional antiserum to the 17 mer and two antisera to synthetic hcrt2.

In immunohistochemical studies with antiserum 2050 on sections from perfused adult male rats, immunoreactive cell bodies were observed exclusively in the perifornical nucleus and dorsal and lateral hypothalamic areas, consistent with the in situ hybridization results (FIG. 4). This coincident staining, its elimination when the serum was preincubated with the peptide immunogen, and the very low nonspecific background observed, together with the Western blot results, provided strong evidence for the specificity of the antiserum for hypocretin. In addition to cell bodies, the serum detected a prominent network of fibers located within the hypothalamus, particularly the posterior region. Less prominent fiber projections were observed in apparent terminal fields within the preoptic area, the medial dorsal and reuniens nuclei of the thalamus, the dorsal raphe nucleus, the locus coeruleus, the laterodorsal tegmental nucleus, the central gray, the colliculi and the nucleus of the solitary tract. In immuno-electron microscopy studies, immunoreactive secretory vesicles were observed.

EXAMPLE 6

Figure 7A:
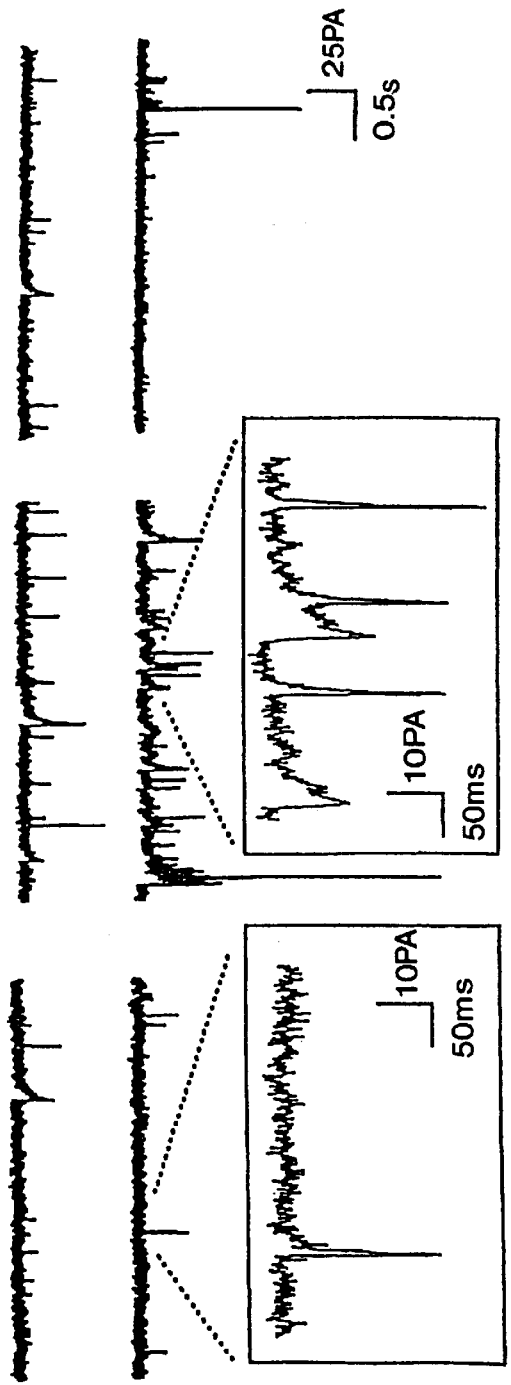
FIGS. 7A–7B are graphical representation of the results of voltage clamp experiments on isolated in vitro rat hypothalamic cells, in which application of 1 μg hcrt2 produced electrical responses in adult but not immature neurons.

The putative structures of the hypocretins, their expression within the dorsolateral hypothalamus and accumulation within fibers and vesicles suggested that they may have intercellular signaling activity. To test this hypothesis, 10-day cultures of synaptically-coupled rat hypothalamic neurons were prepared and postsynaptic currents were recorded under voltage clamp. Application of a synthetic peptide corresponding to amidated hcrt2 at 1 $\mu$M evoked a substantial, but reversible, increase in the frequency of postsynaptic currents in 75% of the neurons tested (FIG. 7A), indicating an increase in the activity of presynaptic axons, and suggesting an increase in excitation. The other 25% of the cells showed no response to hcrt2. There was little response by hypothalamic neurons that had been in culture for only 3–5 days, suggesting that a certain degree of synaptic maturity was required for the effect. Hcrt2 elicited no response from synaptically coupled hippocampal dentate granule neurons in culture, demonstrating target selectivity and suggesting that specific receptors for hcrt2 may exist.

EXAMPLE 7

Synthetic, amidated hcrt2 peptide at different concentrations was infused intracerebroventricularly in rats and body temperature by was monitored telemetry. Stereotactic ablation studies have previously implicated the dorsal-lateral hypothalamus in feeding behavior, blood pressure, and central regulation of immune function, although precise nuclei have not been correlated with these activities. A threshold-type response was obtained in which, at the highest dose, 10 $\mu$g, body temperature dropped from 37.7 to 36.7 degrees Celsius over 30 minutes following administration, then recovered to normal over 2 hours. Food intake was monitored over 2 hours following administration and a 40% reduction in food intake was measured at a dose of 5 $\mu$g. Whereas the concentrations of peptide required for an effect might seem high, they are comparable to the doses of leptin administered ICV to obtain a comparable suppression of food intake. The presumed target cells of hypocretin may not be very accessible by this unphysiological mode of administration. Local injection or intravenous administration of hypocretin might be more suitable for physiological studies.

The cell bodies that produce the hypocretins are located in an area implicated in ablation studies as regulatory centers for appetitive behaviors, suggesting that the hypocretins may serve as a major transmitters for the central system signalling the status of energy balance in the major fat repositories. The projections of hypocretin-producing cells indicate that the peptides function both within the hypothalamus and at a complex and diffuse network of targets in several regions of the brain that may coordinate the various aspects of appetitive behavior, adaptive thermogenesis and metabolic regulation.

Rat hypothalamus from 18-day embryos was cultured for 10 days in vitro. The mediobasal hypothalamus was removed from embryonic day 18 Sprague Dawley rats. The tissue was enzymatically digested in a mild protease solution (10 U/ml papain and 0.2 mg/ml L-cysteine in Earle's balanced salt solution) for 30 minutes. Next, the tissue was pelleted, and the protease solution was removed. Tissue was then suspended in standard tissue culture medium (glutamate- and glutamate-free DMEM supplemented with 10% fetal bovine serum, 100 U/ml penicillin/streptomycin, and 6 gm/l glucose) and then triturated into a single-cell suspension. Cells were washed and pelleted an additional three times. The single-cell suspension was plated onto 22 mm$^2$ glass coverslips that had been coated with high-molecular-weight (540,000 Da) poly-D-lysine. High-density cultures (200,000/cm$^2$) were used for all experiments. Hypothalamic neural cultures were maintained in a Napco 3600 incubator (37 degree Celsius and 5% $CO_2$) until they were ready for use. To limit non-neuronal cell proliferation cytosine arabinofuranoside (1 $\mu$M) was added to the tissue culture medium 1 day after plating.

Figure 7B:
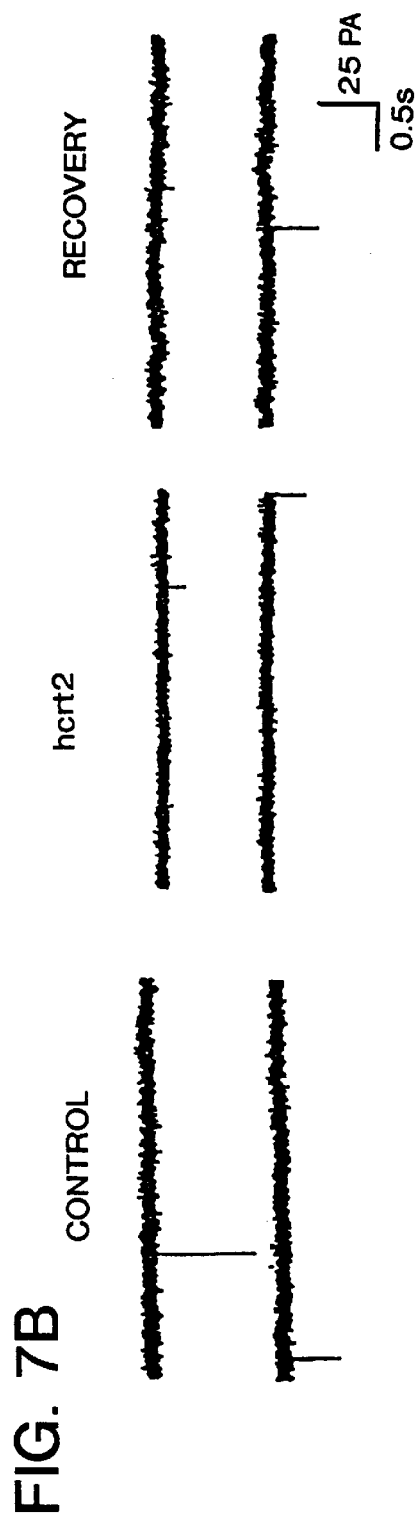

Synaptically coupled hypothalamic neurons were recorded in voltage clamp with a whole cell pipette (holding potential=−60 mV). This recording is typical of 9 of 12 cells examined under these conditions. The frequency of postsynaptic events (PSCs) was greatly increased (up to +400%) by 1 $\mu$M hcrt2 applied to the bath. After washout of the peptide, the frequency of PSCs returned to normal baseline levels. Inset boxes show higher resolution of the events indicated by the dotted line. Both boxes (in FIGS. 7A and B) were recorded with an identical delay after hcrt2 administration. A less mature hypothalamic neuron after 4 days of culture was unresponsive to 1 $\mu$M hcrt2 (FIG. 7B). Pipette solution contained 128 mM $KMeSO_4$, 27 mM KCl, 0.4 mM EGTA, 1 mM ATP, and 0.5 mM GTP.

The preceding written description provides a full, clear, concise and exact disclosure of the invention so as to enable one skilled in the art to make and use the same. This disclosure should not be construed so as to impart any direct or implied limitation upon the scope of the invention which is particularly pointed out and distinctly claimed below.

TABLE 1

Cumulative Data From 100 Clones

| Clone[a] | BLAST Homology[b] | Accession#[c] | #[d] | Pattern[e] |
|---|---|---|---|---|
| 2 + | oxytocin | M25649 | 13 | A/A |
| 6 + | VAT1-like | T05306 | 11 | B/B |
| 1 + | CART | U10071 | 7 | C |
| 35 + | novel | | 6 | A/A |
| 15 + | novel | | 4 | B/C |
| 25 + | POMC | J00759 | 4 | A |
| 12 + | novel(E) | R75926 | 3 | B/B |
| 16 + | vasopressin | M25646 | 3 | A |
| 18 + | glutathione perox | U13705 | 3 | B |
| 29 + | novel CaM kinase | | 3 | B/C |
| 3 + | novel | | 2 | B/C |
| 10 + | novel | | 2 | B/B |
| 51 + | ubiquitin carrier | M91679 | 2 | C |
| 62 + | novel | | 2 | C |
| 5 − | calbindin | U08290 | | B |
| 14 + | melanin-conc hormone | M62641 | | C |
| 17 + | asp aminotrans | M18467 | | D |
| 19 − | novel(E) | R74893 | | D |
| 20 + | novel | | | A/B |
| 21 − | novel(E) | T32756 | | A/D |
| 22 − | novel | | | D |
| 33 − | novel(E) | R67552 | | A/A |
| 34 − | Cl/HCO₃ exchanger | J05167 | | C |
| 37 + | novel | | | B/D |
| 39 − | novel | | | C |
| 45 + | novel | | | C |
| 46 + | fibromodulin | X82152 | | C |
| 47 | perox enolhydratase | U08976 | | C |
| 48 + | galanin | J03624 | | B |

TABLE 1-continued

Cumulative Data From 100 Clones

| Clone[a] | BLAST Homology[b] | Accession#[c] | #[d] | Pattern[e] |
|---|---|---|---|---|
| 52 − | 5-HT₂ receptor | L31546 | | B |
| 53 + | MHC orf | M32010 | | E |
| 55 + | HNF dimer cofactor | M83740 | | C |
| 56 + | carbonyl reductase | X84349 | | C |
| 57 + | tyrosine hydroxylase | M10244 | | A |
| 63 + | novel | | | D |
| 67 + | novel | | | B/B |
| 73 + | novel | | | C |
| 74 + | novel(E) | T93996 | | C |
| 75 + | lamin C2 | D14850 | | A |
| 86 + | novel | | | C |
| 92 − | novel(E) | R49544 | | C |
| 98 + | novel | | | B/D |
| 99 − | neuronal kinesin | U06698 | | B/D |

[a]number of prototype clone in set of 100 followed by indication (+/−) as to whether 3' sequence contained poly(A)-addition hexad (no 3' sequence for clone 47)

[b]short name of matching species or novel for no match:(E) indicates EST match

[c]GenBank database reference

[d]number of representatives in set of 100

[e]hybridization pattern in cDNA library Southern assay/Northern blot assay. Code:A, target only; B, target highly enriched; C, hypothalamus and hippocampus; D, not highly enriched; E, too faint to categorize

We claim:

1. A polynucleotide comprising the sequence of SEQ ID NO:5.

2. A vector comprising the sequence of SEQ ID NO:5.

3. An isolated host cell transfected with the vector of claim 2.

4. An isolated polynucleotide selected from the group consisting of SEQ ID NO: 14 and SEQ ID NO: 3.

5. An isolated polynucleotide selected from the group consisting of SEQ ID NO: 15 and SEQ ID NO: 4.

6. An isolated nucleic acid molecule comprising a nucleotide sequence selected from the group consisting of:

a)
TAAGACGACG GCCTCAGACT TCTTGGGTAT
TTGGACCACT GCACTGAAGA GATCATCTCT
CCAGATTACT TTCCCCTGAG CTCCAGGCAC
CATGAACTTT CCTTCTACAA AGGTTCCCTG
GGCCGCCGTG ACGCTGCTGC TGCTGCTACT
GCTGCCACCG GCGCTGCTGT CGCTTGGGGT
GGACGCACAG CCTCTGCCCG ACTGCTGTCG
CCAGAAGACG TGTTCCTGCC GTCTCTACGA
ACTGTTGCAC GGAGCTGGCA ACCACGCTGC
GGGTATCCTG ACTCTGGGAA AGCGGCGGCC
TGGACCTCCA GGCCTCCAGG GACGGCTGCA
GCGCCTCCTT CAGGCCAACG GTAACCACGC
AGCTGGCATC CTGACCATGG GCCGCCGCGC
AGGCGCAGAG CTAGAGCCAC ATCCCTGCTC
TGGTCGCGGC TGTCCGACCG TAACTATCAC
CGCTTTAGCA CCCCGGGGAG GGTCCGGAGT
TTGAACCCAT CTTCTATCCT TGTCCTGATC
CAAACTTCCC CCTCTGCTCG CCGCTGTCAG
TCTCTTGGTA AATGGCAATA AAGACGTTTC
TCTGTTGGTG TG (SEQ ID NO: 4); and b) the complement of SEQ ID NO: 4.

* * * * *

SEQUENCE LISTING

<160> NUMBER OF SEQ ID NOS: 29

<210> SEQ ID NO 1
<211> LENGTH: 130
<212> TYPE: PRT
<213> ORGANISM: ratus ratus

<400> SEQUENCE: 1

Met Asn Leu Pro Ser Thr Lys Val Pro Trp Ala Ala Val Thr Leu Leu
1               5                   10                  15

Leu Leu Leu Leu Leu Pro Pro Ala Leu Leu Ser Leu Gly Val Asp Ala
                20                  25                  30

Gln Pro Leu Pro Asp Cys Cys Arg Gln Lys Thr Cys Ser Cys Arg Leu
                35                  40                  45

Tyr Glu Leu Leu His Gly Ala Gly Asn His Ala Ala Gly Ile Leu Thr
        50                  55                  60

Leu Gly Lys Arg Arg Pro Gly Pro Pro Gly Leu Gln Gly Arg Leu Gln
65                  70                  75                  80

Arg Leu Leu Gln Ala Asn Gly Asn His Ala Ala Gly Ile Leu Thr Met
                85                  90                  95

Gly Arg Arg Ala Gly Ala Glu Leu Glu Pro Tyr Pro Cys Pro Gly Arg

Arg Cys Pro Thr Ala Thr Ala Thr Ala Leu Ala Pro Arg Gly Gly Ser
        115                 120                 125

Arg Val
    130

<210> SEQ ID NO 2
<211> LENGTH: 130
<212> TYPE: PRT
<213> ORGANISM: mus musculus

<400> SEQUENCE: 2

Met Asn Phe Pro Ser Thr Lys Val Pro Trp Ala Ala Val Thr Leu Leu
 1               5                  10                  15

Leu Leu Leu Leu Leu Pro Pro Ala Leu Leu Ser Leu Gly Val Asp Ala
                20                  25                  30

Gln Pro Leu Pro Asp Cys Cys Arg Gln Lys Thr Cys Ser Cys Arg Leu
            35                  40                  45

Tyr Glu Leu Leu His Gly Ala Gly Asn His Ala Ala Gly Ile Leu Thr
    50                  55                  60

Leu Gly Lys Arg Arg Pro Gly Pro Gly Leu Gln Gly Arg Leu Gln
65                  70                  75                  80

Arg Leu Leu Gln Ala Asn Gly Asn His Ala Ala Gly Ile Leu Thr Met
                85                  90                  95

Gly Arg Arg Ala Gly Ala Glu Leu Glu Pro His Pro Cys Ser Gly Arg
            100                 105                 110

Gly Cys Pro Thr Val Thr Thr Thr Ala Leu Ala Pro Arg Gly Gly Ser
        115                 120                 125

Gly Val
    130

<210> SEQ ID NO 3
<211> LENGTH: 569
<212> TYPE: DNA
<213> ORGANISM: ratus ratus

<400> SEQUENCE: 3
taagacgacg gcctcagact ccttgggtat ttggaccact gcaccgaaga taccatctct      60
ccggattacc tctccctgag ctccagacac catgaacctt ccttctacaa aggttccctg     120
ggccgccgtg acgctgctgc tgctgctact gctgccgccg gcgctgctgt cgcttggggt     180
ggacgcgcag cctctgcccg actgctgtcg ccagaagacg tgttcctgcc ggctctacga     240
actgttgcac ggagctggca accacgccgc gggcatcctc actctgggaa agcggcgacc     300
tggaccccca ggcctccaag gacggctgca gcgcctcctt caggccaacg gtaaccacgc     360
agctggcatc ctgaccatgg gccgccgcgc aggcgcagag ctagagccat atccctgccc     420
tggtcgccgc tgtccgactg caaccgccac cgctttagcg cccgggggcg gatccagagt     480
ctgaacccgt cttctatccc tgtcctagtc ctaactttcc cctctcctcg ccagtcccta     540
ggcaataaag acgtttctct gttggtgtg                                       569

<210> SEQ ID NO 4
<211> LENGTH: 582
<212> TYPE: DNA
<213> ORGANISM: mus musculus

<400> SEQUENCE: 4

```
taagacgacg gcctcagact tcttgggtat ttggaccact gcactgaaga gatcatctct      60
ccagattact ttcccctgag ctccaggcac catgaacttt ccttctacaa aggttccctg     120
ggccgccgtg acgctgctgc tgctgctact gctgccaccg gcgctgctgt cgcttggggt     180
ggacgcacag cctctgcccg actgctgtcg ccagaagacg tgttcctgcc gtctctacga     240
actgttgcac ggagctggca accacgctgc gggtatcctg actctgggaa agcggcggcc     300
tggacctcca ggcctccagg gacggctgca gcgcctcctt caggccaacg gtaaccacgc     360
agctggcatc ctgaccatgg gccgccgcgc aggcgcagag ctagagccac atccctgctc     420
tggtcgcggc tgtccgaccg taactatcac cgctttagca ccccggggag ggtccggagt     480
ttgaacccat cttctatcct tgtcctgatc caaacttccc cctctgctcg ccgctgtcag     540
tctcttggta aatggcaata aagacgtttc tctgttggtg tg                        582

<210> SEQ ID NO 5
<211> LENGTH: 1458
<212> TYPE: DNA
<213> ORGANISM: ratus ratus

<400> SEQUENCE: 5
gctaggagac attgcggcgg cggtggcggc gttggcagca gctgcagaca tgctgctgct     60
caagaaacag acgaggaca tcagcagtgt ctatgagatc cgggagaagc tgggctcggg    120
tgccttctct gaggtgatgc tggcccagga aggggctct gctcatcttg tggccctcaa     180
gtgcattccc aagaaagcac ttcggggcaa ggaggccctg gtggagaatg agatcgcagt    240
actccgcagg attagccacc ccaacattgt ggctctggag gacgtccacg agagcccttc    300
ccatctctac ttggccatgg agctggtaac aggtggtgaa ctgttgacc gaatcatgga    360 gcggggctcc tacacagaga aggatgcgag ccaccttgta gggcaggtcc ttggtgctgt    420
ctcctacctt catagcctgg gcatcgtgca ccgggacctc aagcctgaaa acctcctcta    480
tgccacacct tttgaggact ccaagatcat ggtctctgac tttggcctgt ccaaaattca    540
agctggcaac atgctaggca cagcctgtgg gaccccagga tatgtggccc cagagctcct    600
ggagcagaaa ccctacggga aggccgtaga tgtgtgggcc ctgggtgtca tctcctacat    660
cctgctgtgt gggtaccccc ccttctatga tgagagcgat cctgaactct tcagccagat    720
tctgagggcc agctacgagt ttgactctcc cttttgggat gacatctcag aatcagccaa    780
agacttcatt cggcaccttc tggaacgtga tcccccagaag aggttcacct gccaacaggc    840
cttacagcat ctctggatct ctggggatgc agccttggac agggacatcc taggttctgt    900
cagtgagcag atccagaaga attttgccag gaccccactgg aagcgtgcat tcaatgccac    960
atcattccta cgtcacatcc gtaagctggg acagagccca gagggtgagg aggcctccag   1020
gcagggtatg acccgtcaca gccacccagg ccttgggact agccagtctc ccaagtggtg   1080
acaaccaggt ggatgccaag gaaggccaag tggactgact cctagctttt ctttcctcca   1140
gcccttttga tctccttccc tgatccttgt ccccgggact ggcctctgtt ggaaagtcca   1200
agaccgtggg tgtgatgcat ggcactgggg tatgggcttt cccaagtatg tccccagcct   1260
ctgtcctttg ttgctgccac cctctatgga aactgaggag gtattcaaaa atggatttgg   1320
gggccatcct tcctgcacct tgcacgcaca tatgcattgc gtggctgttc tgtgctttgc   1380
tgactgtggg tggtcctgct tgtgttgtag cccttagtt cctcctctttt ccaaccaata   1440 aagacaaaca gaacaatg                                                  1458
```

-continued

```
<210> SEQ ID NO 6
<211> LENGTH: 103
<212> TYPE: PRT
<213> ORGANISM: ratus ratus

<400> SEQUENCE: 6

Leu Gly Val Asp Ala Gln Pro Leu Pro Asp Cys Cys Arg Gln Lys Thr
1               5                   10                  15

Cys Ser Cys Arg Leu Tyr Glu Leu Leu His Gly Ala Gly Asn His Ala
            20                  25                  30

Ala Gly Ile Leu Thr Leu Gly Lys Arg Pro Gly Pro Pro Gly Leu
        35                  40                  45

Gln Gly Arg Leu Gln Arg Leu Leu Gln Ala Asn Gly Asn His Ala Ala
    50                  55                  60

Gly Ile Leu Thr Met Gly Arg Arg Ala Gly Ala Glu Leu Glu Pro Tyr
65                  70                  75                  80

Pro Cys Pro Gly Arg Arg Cys Pro Thr Ala Thr Ala Thr Ala Leu Ala
                85                  90                  95

Pro Arg Gly Gly Ser Arg Val
            100

<210> SEQ ID NO 7
<211> LENGTH: 39
<212> TYPE: PRT
<213> ORGANISM: ratus ratus

<400> SEQUENCE: 7

Leu Gly Val Asp Ala Gln Pro Leu Pro Asp Cys Cys Arg Gln Lys Thr
1               5                   10                  15

Cys Ser Cys Arg Leu Tyr Glu Leu Leu His Gly Ala Gly Asn His Ala
            20                  25                  30

Ala Gly Ile Leu Thr Leu Gly
        35

<210> SEQ ID NO 8
<211> LENGTH: 38
<212> TYPE: PRT
<213> ORGANISM: ratus ratus

<400> SEQUENCE: 8

Leu Gly Val Asp Ala Gln Pro Leu Pro Asp Cys Cys Arg Gln Lys Thr
1               5                   10                  15

Cys Ser Cys Arg Leu Tyr Glu Leu Leu His Gly Ala Gly Asn His Ala
            20                  25                  30

Ala Gly Ile Leu Thr Leu
        35

<210> SEQ ID NO 9
<211> LENGTH: 28
<212> TYPE: PRT
<213> ORGANISM: ratus ratus

<400> SEQUENCE: 9

Pro Gly Pro Pro Gly Leu Gln Gly Arg Leu Gln Arg Leu Leu Gln Ala
1               5                   10                  15

Asn Gly Asn His Ala Ala Gly Ile Leu Thr Met Gly
            20                  25

<210> SEQ ID NO 10
<211> LENGTH: 27
```

-continued

```
<212> TYPE: PRT
<213> ORGANISM: ratus ratus

<400> SEQUENCE: 10

Pro Gly Pro Pro Gly Leu Gln Gly Arg Leu Gln Arg Leu Leu Gln Ala
 1               5                  10                  15

Asn Gly Asn His Ala Ala Gly Ile Leu Thr Met
            20                  25

<210> SEQ ID NO 11
<211> LENGTH: 20
<212> TYPE: PRT
<213> ORGANISM: ratus ratus

<400> SEQUENCE: 11

Arg Leu Tyr Glu Leu Leu His Gly Ala Gly Asn His Ala Ala Gly Ile
 1               5                  10                  15

Leu Thr Leu Gly
            20

<210> SEQ ID NO 12
<211> LENGTH: 20
<212> TYPE: PRT
<213> ORGANISM: ratus ratus

<400> SEQUENCE: 12

Arg Leu Gln Arg Leu Leu Gln Ala Asn Gly Asn His Ala Ala Gly Ile
 1               5                  10                  15

Leu Thr Met Gly
            20

<210> SEQ ID NO 13
<211> LENGTH: 9
<212> TYPE: PRT
<213> ORGANISM: ratus ratus

<400> SEQUENCE: 13

Gly Asn His Ala Ala Gly Ile Leu Thr
 1               5

<210> SEQ ID NO 14
<211> LENGTH: 393
<212> TYPE: DNA
<213> ORGANISM: ratus ratus

<400> SEQUENCE: 14
atgaaccttc cttctacaaa ggttccctgg gccgccgtga cgctgctgct gctgctactg      60
ctgccgccgg cgctgctgtc gcttggggtg gacgcgcagc tctgcccga ctgctgtcgc     120 cagaagacgt gttcctgccg tctctacgaa ctgttgcacg gagctggcaa ccacgccgcg     180
ggcatcctca ctctgggaaa gcggcgacct ggaccccag gcctccaagg acggctgcag     240
cgcctccttc aggccaacgg taaccacgca gctggcatcc tgaccatggg ccgccgcgca     300
ggcgcagagc tagagccata tccctgccct gtcgccgct gtccgactgc aaccgccacc     360
gctttagcgc cccggggcgg atccagagtc tga                                 393

<210> SEQ ID NO 15
<211> LENGTH: 393
<212> TYPE: DNA
<213> ORGANISM: mus musculus
<220> FEATURE:
<223> OTHER INFORMATION: tag sequence
```

-continued

<400> SEQUENCE: 15

| atgaactttc | cttctacaaa | ggttccctgg | gccgccgtga | cgctgctgct | gctgctactg | 60 |
| ctgccaccgg | cgctgctgtc | gcttggggtg | gacgcacagc | ctctgcccga | ctgctgtcgc | 120 |
| cagaagacgt | gttcctgccg | tctctacgaa | ctgttgcacg | gagctggcaa | ccacgctgcg | 180 |
| ggtatcctga | ctctgggaaa | gcggcggcct | ggacctccag | gcctcagggg | acggctgcag | 240 |
| cgcctccttc | aggccaacgg | taaccacgca | gctggcatcc | tgaccatggg | ccgccgcgca | 300 |
| ggcgcagagc | tagagccaca | tccctgctct | ggtcgcggct | gtccgaccgt | aactatcacc | 360 |
| gctttagcac | cccggggagg | gtccggagtt | tga | | | 393 |

<210> SEQ ID NO 16
<211> LENGTH: 20
<212> TYPE: DNA
<213> ORGANISM: Artificial Sequence
<220> FEATURE:
<223> OTHER INFORMATION: tag sequence

<400> SEQUENCE: 16
aggccaagaa ttcggcacga                                              20

<210> SEQ ID NO 17
<211> LENGTH: 17
<212> TYPE: DNA
<213> ORGANISM: mus musculus

<400> SEQUENCE: 17
taagacgacg gcctcag                                                 17

<210> SEQ ID NO 18
<211> LENGTH: 18
<212> TYPE: DNA
<213> ORGANISM: mus musculus

<400> SEQUENCE: 18
cacaccaaca gagaaacg                                                18

<210> SEQ ID NO 19
<211> LENGTH: 18
<212> TYPE: DNA
<213> ORGANISM: Artificial Sequence
<220> FEATURE:
<223> OTHER INFORMATION: tag sequence

<400> SEQUENCE: 19
aactggaaga attcgcgg                                                18

<210> SEQ ID NO 20
<211> LENGTH: 14
<212> TYPE: PRT
<213> ORGANISM: mus musculus

<400> SEQUENCE: 20

Arg Leu Leu Leu Gly Asn His Ala Ala Gly Ile Leu Thr Gly
 1               5                  10

<210> SEQ ID NO 21
<211> LENGTH: 36
<212> TYPE: PRT
<213> ORGANISM: ratus ratus

<400> SEQUENCE: 21

His Ser Asp Gly Thr Phe Thr Ser Lys Leu Ser Arg Leu Arg Asp Ser
 1               5                  10                  15

Ala Arg Leu Gln Arg Leu Leu Gln Gly Leu Val His Ser Asp Gly Thr
             20                  25                  30

Phe Thr Ser Lys
         35

<210> SEQ ID NO 22
<211> LENGTH: 41
<212> TYPE: DNA
<213> ORGANISM: ratus ratus

<400> SEQUENCE: 22
atcgagatct agacaccatg aaccttcctt ctacaaaggt t                41

<210> SEQ ID NO 23
<211> LENGTH: 68
<212> TYPE: DNA
<213> ORGANISM: ratus ratus

<400> SEQUENCE: 23
actgtctaga tcatagatct tcttcagaaa taagtttttg ttcgactctg gatccgcccc    60
ggggcgct                                                             68

<210> SEQ ID NO 24
<211> LENGTH: 31
<212> TYPE: DNA
<213> ORGANISM: ratus ratus

<400> SEQUENCE: 24
atcgagatct cttggggtgg acgcgcagcc t                            31

<210> SEQ ID NO 25
<211> LENGTH: 30
<212> TYPE: DNA
<213> ORGANISM: ratus ratus

<400> SEQUENCE: 25
actgaattct cagactctgg atccgccccg                              30

<210> SEQ ID NO 26
<211> LENGTH: 20
<212> TYPE: DNA
<213> ORGANISM: mus musculus

<400> SEQUENCE: 26
gacggcctca gacttcttgg                                         20

<210> SEQ ID NO 27
<211> LENGTH: 20
<212> TYPE: DNA
<213> ORGANISM: mus musculus

<400> SEQUENCE: 27
gcaacagttc gtagagacgg                                         20

<210> SEQ ID NO 28
<211> LENGTH: 17
<212> TYPE: PRT
<213> ORGANISM: ratus ratus

<400> SEQUENCE: 28

Cys Pro Thr Ala Thr Ala Thr Ala Cys Ala Pro Arg Gly Gly Ser Arg
1               5                   10                  15

Val

<210> SEQ ID NO 29
<211> LENGTH: 358
<212> TYPE: PRT
<213> ORGANISM: ratus ratus

<400> SEQUENCE: 29

Met Leu Leu Leu Lys Lys Gln Thr Glu Asp Ile Ser Ser Val Tyr Glu
1               5                   10                  15

Ile Arg Glu Lys Leu Gly Ser Gly Ala Phe Ser Glu Val Met Leu Ala
                20                  25                  30

Gln Glu Arg Gly Ser Ala His Leu Val Ala Leu Lys Cys Ile Pro Lys
            35                  40                  45

Lys Ala Leu Arg Gly Lys Glu Ala Leu Val Glu Asn Glu Ile Ala Val
        50                  55                  60

Leu Arg Arg Ile Ser His Pro Asn Ile Val Ala Leu Glu Asp Val His
65                  70                  75                  80

Glu Ser Pro Ser His Leu Tyr Leu Ala Met Glu Leu Val Thr Gly Gly
                85                  90                  95

Glu Leu Phe Asp Arg Ile Met Glu Arg Gly Ser Tyr Thr Glu Lys Asp
            100                 105                 110

Ala Ser His Leu Val Gly Gln Val Leu Gly Ala Val Ser Tyr Leu His
        115                 120                 125

Ser Leu Gly Ile Val His Arg Asp Leu Lys Pro Glu Asn Leu Leu Tyr
130                 135                 140

Ala Thr Pro Phe Glu Asp Ser Lys Ile Met Val Ser Asp Phe Gly Leu
145                 150                 155                 160

Ser Lys Ile Gln Ala Gly Asn Met Leu Gly Thr Ala Cys Gly Thr Pro
                165                 170                 175

Gly Tyr Val Ala Pro Glu Leu Leu Glu Gln Lys Pro Tyr Gly Lys Ala
            180                 185                 190

Val Asp Val Trp Ala Leu Gly Val Ile Ser Tyr Ile Leu Leu Cys Gly
        195                 200                 205

Tyr Pro Pro Phe Tyr Asp Glu Ser Asp Pro Glu Leu Phe Ser Gln Ile
210                 215                 220

Leu Arg Ala Ser Tyr Glu Phe Asp Ser Pro Phe Trp Asp Asp Ile Ser
225                 230                 235                 240

Glu Ser Ala Lys Asp Phe Ile Arg His Leu Leu Glu Arg Asp Pro Gln
                245                 250                 255

Lys Arg Phe Thr Cys Gln Gln Ala Leu Gln His Leu Trp Ile Ser Gly
            260                 265                 270

Asp Ala Ala Leu Asp Arg Asp Ile Leu Gly Ser Val Ser Glu Gln Ile
        275                 280                 285

Gln Lys Asn Phe Ala Arg Thr His Trp Lys Arg Ala Phe Asn Ala Thr
        290                 295                 300

Ser Phe Leu Arg His Ile Arg Lys Leu Gly Gln Ser Pro Glu Gly Glu
305                 310                 315                 320

Glu Ala Ser Arg Gln Gly Met Thr Arg His Ser His Pro Gly Leu Gly
                325                 330                 335

Thr Ser Gln Ser Pro Lys Trp Val Thr Thr Arg Trp Met Pro Arg Lys
            340                 345                 350

```
Ala Lys Trp Thr Asp Ser
        355
```